United States Patent [19]

Hartman et al.

[11] Patent Number: 4,742,004

[45] Date of Patent: May 3, 1988

[54] METHOD FOR PRODUCING ENZYMATICALLY ACTIVE EUCARYOTIC SOD IN BACTERIA

[75] Inventors: Jacob R. Hartman, Holon; Dov Kanner, Rehovot; Daniel Bartfeld, Nes Ziona, all of Israel

[73] Assignee: BIO-Technology General Corp., New York, N.Y.

[21] Appl. No.: 644,105

[22] Filed: Aug. 27, 1984

[51] Int. Cl.4 .................. C12P 21/02; C12N 15/00; C12N 9/02

[52] U.S. Cl. .................. 435/70; 435/172.3; 435/189; 935/9; 935/14

[58] Field of Search .................. 435/70, 172.3, 189; 935/9, 14

[56] References Cited

U.S. PATENT DOCUMENTS 3,579,495 5/1971 Huber .
4,340,675 7/1982 Johansen .................. 435/189
4,390,628 6/1983 Johansen .................. 435/189

OTHER PUBLICATIONS

Lieman-Hurwitz et al., P.N.A.S. 79:2808-2811, 1982 (May).
Lehninger, In *Biochemistry*, 2nd Ed., Worth Publishers, 1975.
Hartz, J. W. et al., J. Biol. Chem. 247: 7043 (1972).
Jabusch, J. R. et al., Biochemistry 19: 2310 (1980).
Barra et al., FEBS Letters 120: 53 (1980).
McCord, J. M. et al., J. Biol. Chem. 244: 6049 (1969).
Fridovich, I., *Advances in Inorganic Biochemistry*, (Eichhorn and Marzilli, eds.) (Elsevier/North Holland, New York) pp. 67-90 (1979).
Freeman, B. A. et al., Laboratory Investigation 47: 412 (1982).
Steinman, H. M., *Superoxide Dismutase*, (Oberly, ed.) CRC Press, Florida, pp. 11-68 (1982).
Sherman, L. et al., Proc. Natl. Acad. Sci. USA 80: 5465 (1983).
Huber, W. et al., Clinics in Rheum. Dis. 6: 465 (1980).
McCord, J. M., Can. J. Physiol. Pharma. 60: 1346 (1982).
Alvarez, J. G. et al., Biol. Reprod. 28: 1129 (1983).
Talmasoff, J. M. et al., Proc. Natl. Acad. Sci. USA 77: 2777 (1980).

*Primary Examiner*—Thomas G. Wiseman
*Assistant Examiner*—Thomas D. Mays
*Attorney, Agent, or Firm*—John P. White

[57] ABSTRACT

A method of producing enzymatically active eucaryotic superoxide dismutase or an analog thereof in a bacterial cell which contains and is capable of expressing a DNA sequence encoding the superoxide dismutase or analog thereof comprising maintaining the bacterial cell under suitable conditions and in a suitable production medium. The production medium is supplemented with an amount of Cu++ so that the concentration of Cu++ in the medium is greater than about about 2 ppm.

The invention also concerns methods of recovering purified enzymatically active eucaryotic superoxide dismutase or analogs from bacterial cells producing the superoxide dismutase or analog.

15 Claims, 24 Drawing Sheets

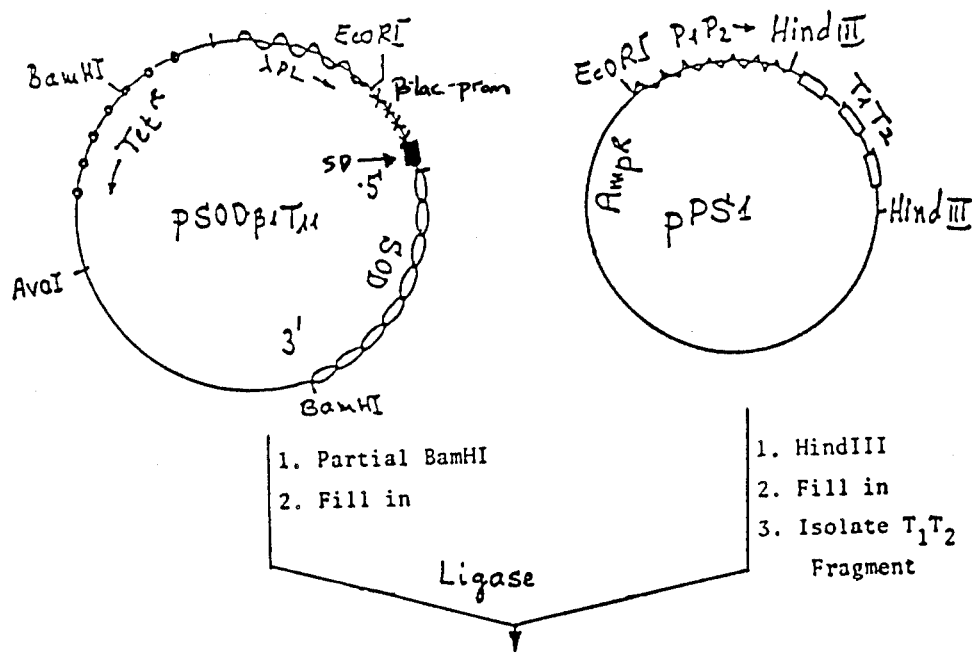
Fig. 16
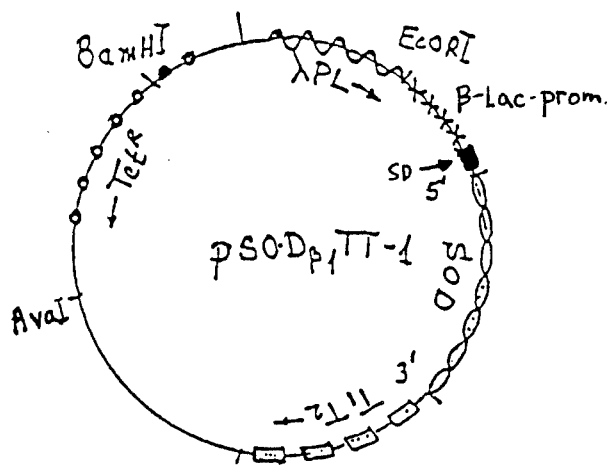

Fig. 21
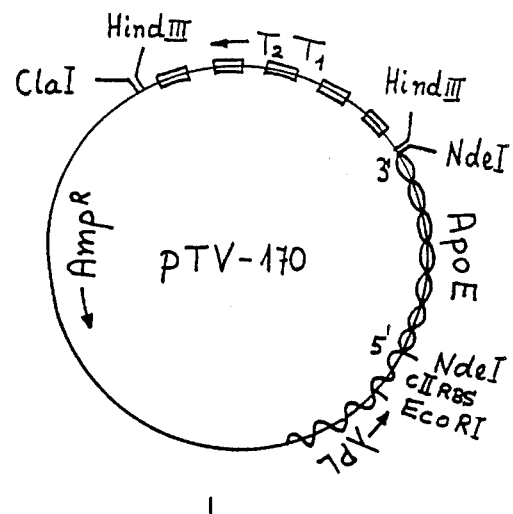
1. Partial NdeI
2. Fill in
3. Ligase
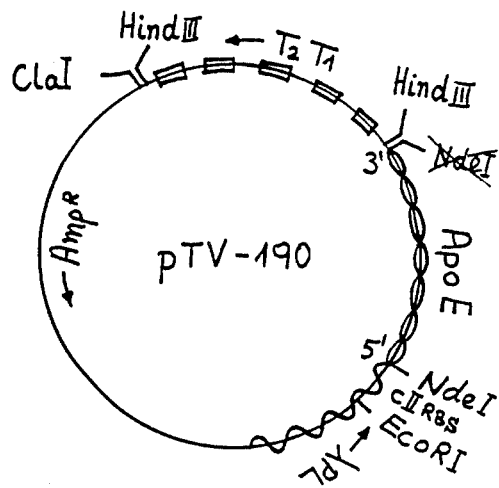

Fig. 22
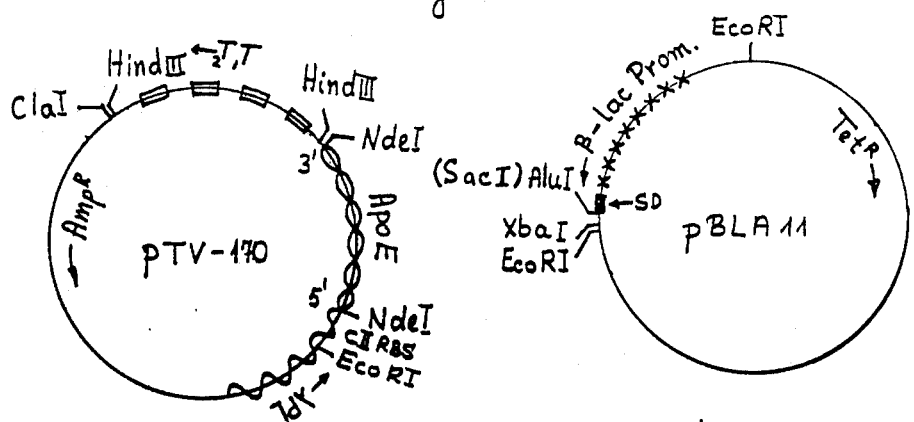
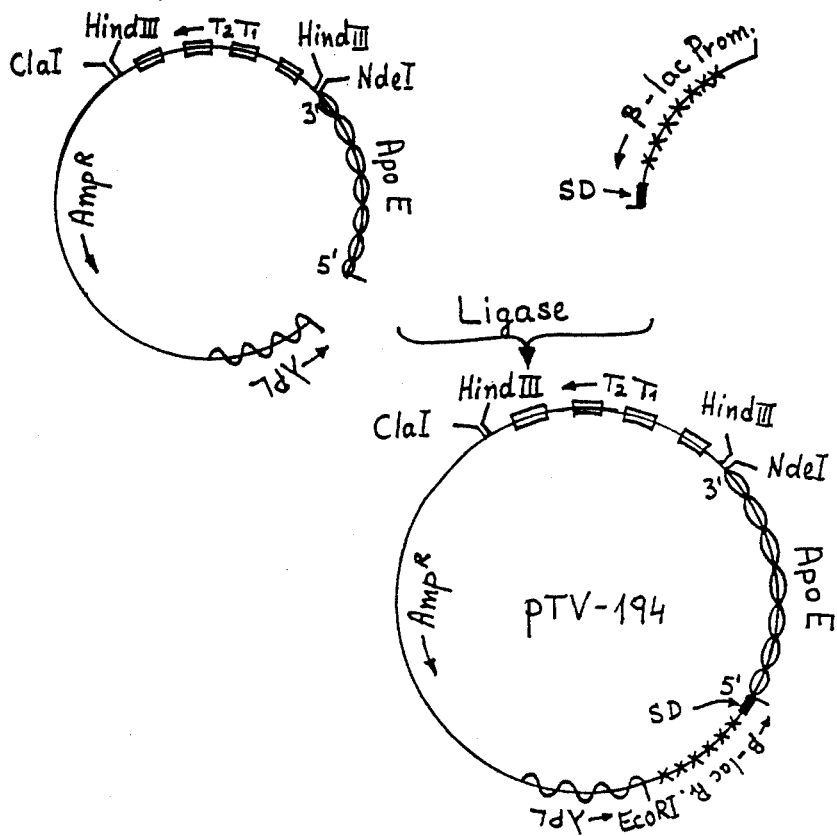

METHOD FOR PRODUCING ENZYMATICALLY ACTIVE EUCARYOTIC SOD IN BACTERIA

BACKGROUND OF THE INVENTION

Throughout this application various publications are referenced by arabic numerals within parentheses. Full citations for these references may be found at the end of the specification immediately preceding the claims. The disclosures of these publications in their entireties are hereby incorporated by reference into this application in order to more fully describe the state of art as known to those skilled therein as of the date of the invention described and claimed herein.

Superoxide dismutase (SOD) and the phenomenon of oxygen free radicals ($O_2^-$) was discovered in 1968 by McCord and Fridovich (1). Superoxide radicals and other highly reactive oxygen species are produced in every respiring cell as by-products of oxidative metabolism, and have been shown to cause extensive damage to a wide variety of macromolecules and cellular components (for review see 2,3). A group of metalloproteins known as superoxide dismutases catalyze the oxidation-reduction reaction $2O_2^- + 2H^+ \rightarrow H_2O_2 + O_2$ and thus provide a defense mechanism against oxygen toxicity. There are three known forms of SODs containing different metals in the protein molecules namely iron, manganese or both copper and zinc. All of them catalyze the same reaction with ultimate efficiency, and all operate by a similar mechanism in which the metal is the catalytic factor in the active site. These enzymes fall into several evolutionary groups. The Mn and Fe-SODs are found primarily in prokaryotic cells while CuZn-SOD have been demonstrated in virtually all eucaryotic organisms (4). Human Cu/Zn SOD-1 is a dimeric metallo-protein composed of identical non-covalently linked subunits, each having a molecular weight of 16000 daltons and containing one atom of copper and one of zinc (5). Each subunit is composed of 153 amino acids whosesequence was established (6,7). Furthermore, a cDNA clone containing the entire coding region of human SOD-1 was recently isolated and sequenced (8,9).

The human Cu-Zn SOD analog produced differs from natural human Cu-Zn SOD in that the amino terminus alanine is not acetylated. The natural human SOD is acetylated at the amino terminus alanine (Hartz, J. W. and Deutsch, H. F., J. Biol. Chem. (1972) 247, 7043–7050, Jabusch, J. R., et al., Biochemistry (1980) 19, 2310–2316; Barra, et al., FEBS Letters (1980) 120, 53 and Oberly, L. W. *Superoxide Dismutase*, Vol. I, CRC Press, Florida, (1982), pp. 32–33). The natural human SOD is likely to be glycosylated like bovine SOD (Huber, W., U.S. Pat. No. 3,579,495, issued May 18, 1971). Bacterial-produced human SOD is almost certainly not glycosylated as *Escherichia coli* does not glycosylate proteins which it produces. The amino acid sequence of the bacterial-produced SOD analog is identical to that of mature human SOD and does not contain a methionine residue at its N-terminus.

Since every biological macromolecule can serve as a target for the damaging action of the abundant superoxide radical, interest has evolved in the therapeutic potential of SOD. The scientific literature suggests that SOD could be useful in a wide range of clinical applications. These include prevention of oncogenesis and of tumor promotion and reduction of cytotoxic and cardiotoxic effects of anticancer drugs (10), anti-inflammatory (11), protection of ischemic tissues (12) and protection of spermatozoa (13). In addition, there is great interest in studying the effect of SOD on the aging process (14).

The exploration of the therapeutic potential of human SOD-1 (EC 1.15.1.1) has been limited mainly due to its scarce availability.

To overcome this problem, we have inserted the SOD cDNA of Groner et al. (8) into efficient bacterial expression vectors (copending U.S. patent filed together with this patent). However, although the bacteria produce large amounts of an analog of human Cu/Zn SOD, most of the protein is lacking enzymatic activity.

This invention provides a method for producing in bacteria and purifying an enzymatically active analog of human Cu/Zn SOD.

SUMMARY OF THE INVENTION

A method of producing enzymatically active eucaryotic superoxide dismutase or an analog thereof in a bacterial cell has been discovered. The bacterial cell contains and is capable of expressing a DNA sequence encoding the superoxide dismutase or analog. The method comprises maintaining the bacterial cell under suitable conditions and in a suitable production medium. The production medium is supplemented with an amount of $Cu^{++}$ so that the concentration of $Cu^{++}$ available to the cell in the medium is greater than about 2 ppm.

In a preferred embodiment of the invention the bacterial cell is an *Escherichia coli* cell containing a plasmid which contains a DNA sequence encoding for an analog of human superoxide dismutase. The concentration of $Cu^{++}$ in the production medium is from about 50 to about 250 ppm.

The invention also concerns a method of recovering purified enzymatically active eucaryotic superoxide dismutase or an analog thereof produced in a bacterial cell in accordance with the methods of this invention. The method comprises isolating the bacterial cell from the growth medium and suspending the bacterial cell in a suitable solution having a pH from about 7.0 to about 8.0. The cell wall of the suspended bacterial cell is disrupted and the resulting homogeneous solution is then sonicated under suitable conditions. The sonicated solution is centrifuged under suitable conditions and the supernatant is removed and heated for about 2 hours at about 65° C. The supernatant is then cooled and centrifuged under suitable conditions to produce a clear supernatant protein solution. The resulting supernatant is concentrated to an appropriate volume and subjected to ion exchange chromatography on a suitable anion exchanger equilibrated at a pH from about 7.0 to about 8.0. The resulting solution containing the superoxide dismutase or analog is collected, concentrated to an appropriate volume and dialyzed against a buffered solution with a pH from about 7.0 to about 8.0. This concentrated buffered solution is subjected to ion exchange chromatography on a suitable anion exchanger equilibrated at a pH from about 7.0 to about 8.0 and the anion exchange-protein complex is subjected to a suitable salt gradient. Fractions containing the superoxide dismutase or analog are collected, concentrated and dialyzed against distilled water. The pH of the solution of interest is adjusted to a pH from about 4.0 to about 5.0 with a suitable buffer. The buffered solution is then subjected to ion exchange chromatography with a suitable cation exchanger equilibrated at a pH from about 4.0 to about 5.0. The protein-cation exchanger complex is subjected to a suitable salt gradient and the resulting fractions which contain the purified superoxide dismutase or analog are collected.

The invention also concerns purified enzymatically active eucaryotic superoxide dismutase or analogs thereof produced by the methods of this invention.

DESCRIPTION OF THE FIGURES

The restriction maps for each of the plasmids shown in FIGS. 1–24 do not identify all restriction sites present on each plasmid. In some cases restriction sites are shown in one figure but not in another. However, in all cases those restriction sites necessary for a complete understanding of the invention are shown.

A plasmid containing bGH cDNA, D4 (ATCC No. 31826), was digested with HaeII. The resulting 1600 base pair large fragment was purified and digested at

```
CCATATGTCCTTGTCCGGCCTGTTTGCCAACGCTGTGCTC—3'
           3'-GCGACACGAGGCCCGAGTCGTGGACGTGGTCGACG
```

37° C. for 5 minutes with S1 exonuclease. A synthetic EcoRI linker with the sequence:

```
GGAATTCC
CCTTAAGG
``` was attached to the ends of the resulting fragments by ligation. The ligation mixture was cleaved with EcoRI and inserted into pBR322 (ATCC No. 37017) which had been cleaved with EcoRI. A clone, pALRI, was obtained which upon cleavage with EcoRI released a 1200 base pair fragment with the sequence:

```
AATTCCCAGCCATG . . .
     GGGTCGGTAC . . .
``` at the 5' end. This sequence demonstrates that pALRI contains an EcoRI restriction site which includes the TTC codon for residue number 1 (phenylalanine) of natural bGH. pALRI was subjected to a partial cleavage with PstI. The digest was treated with DNA polymerase I large fragment (Klenow) and HindIII linkers with the sequence:

```
GAAGCTTC
CTTCGAAG
``` were attached by ligation. The ligation mixture was cleaved with EcoRI and HindIII. The fragment containing bGH cDNA was isolated and subcloned into pBR322 between the EcoRI and HindIII restriction sites to give pAL500 (ATCC No. 39782).

Figure 1:
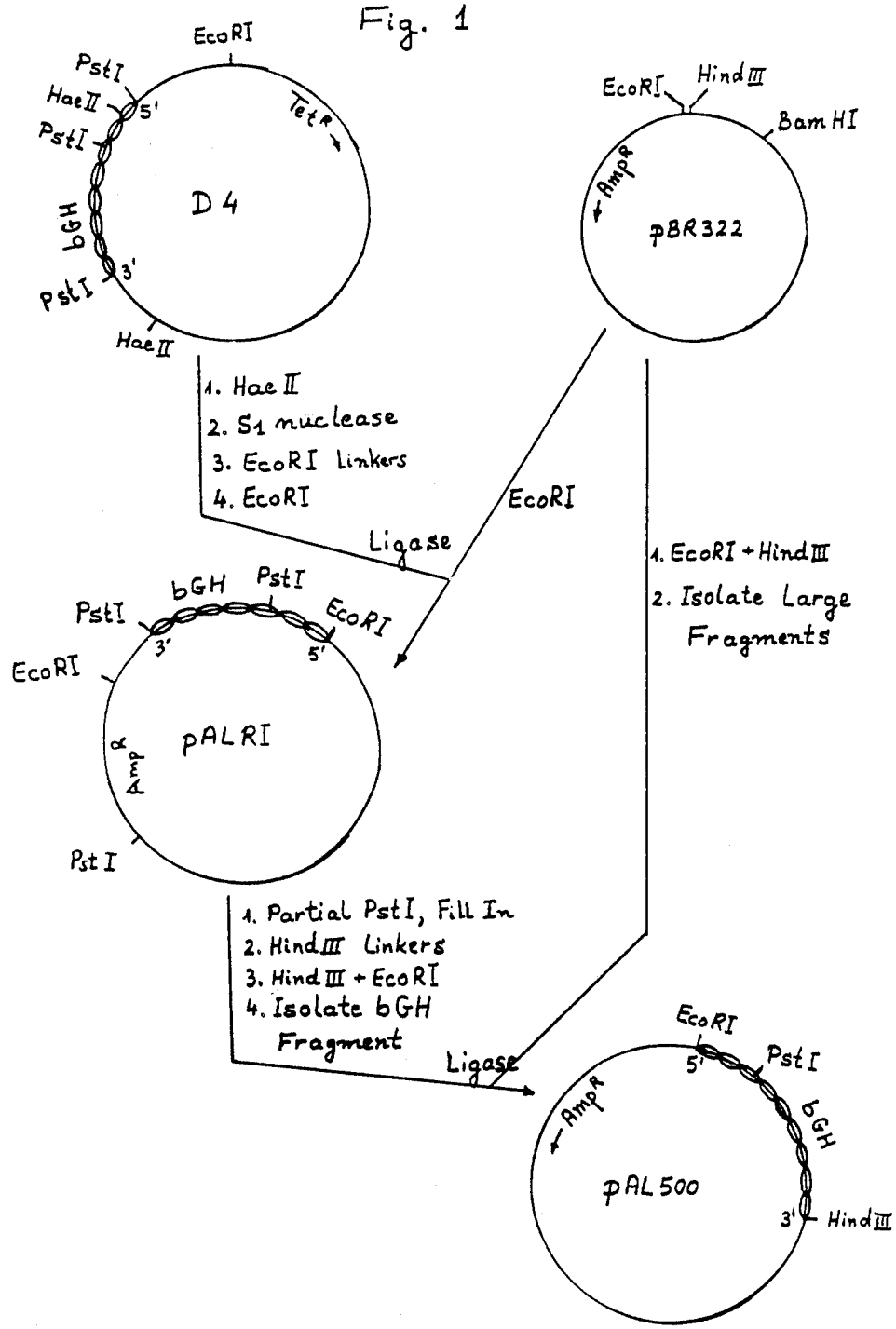
FIG. 1. Construction of pAL500.
Figure 2:
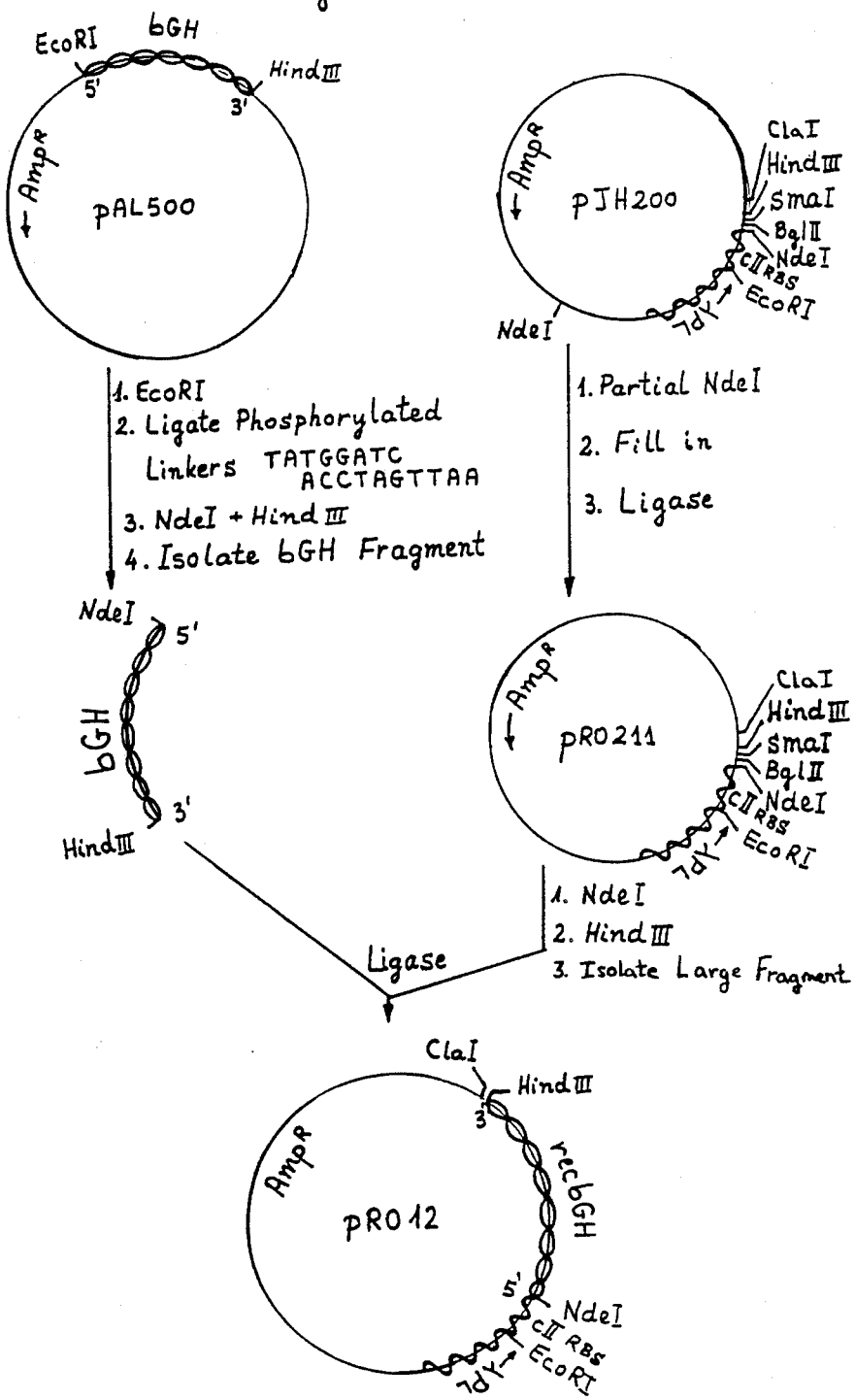

FIG. 2. Construction of pRO211 and pRO12.

The plasmid pJH200 (ATCC No. 39783) was partially digested with NdeI, treated with DNA polymerase I (Klenow) to fill in the ends and the resulting ends were religated to form the expression vector pRO211. The expression vector pRO211 was digested with NdeI and HindIII, the large fragment isolated and ligated to an NdeI-HindIII bGH fragment isolated from pAL500 (ATCC No. 39782) to give pRO12. (The NdeI-HindIII fragment was produced from pAL500 by digesting it with EcoRI and ligating to the ends of the digestion product synthetic linkers with the sequence:

```
TATGGATC
ACCTAGTTAA
```

The ligation mixture was digested with NdeI and HindIII and the resulting NdeI-HindIII bGH fragment isolated.)

Figure 3:
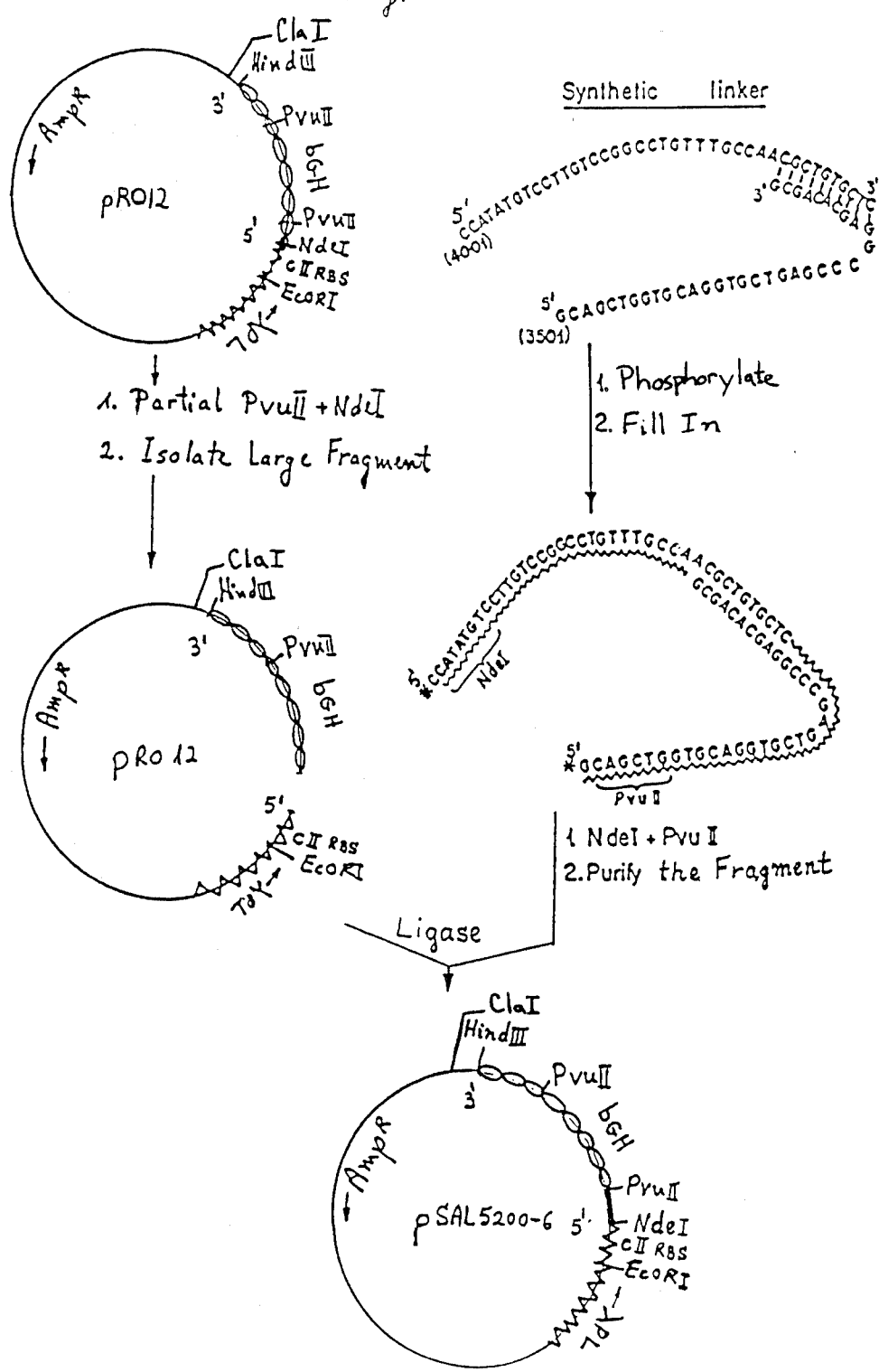

FIG. 3. Construction of pSAL 5200-6.

pRO12 (FIG. 2) was partially digested with PvuII followed by digestion with NdeI to eliminate a 72 base pair fragment. A synthetic DNA fragment coding for the first 24 amino acids of the N-terminus of authentic bGH was ligated to the digested pRO12.

The synthetic DNA fragment was constructed by annealing two phosphorylated synthetic single-stranded DNAs of the sequence:

The annealed fragment was treated with DNA polymerase I (Klenow) in the presence of all four deoxyribonucleoside triphosphates in order to form the full length double-stranded DNA. The fragment was digested with PvuII and NdeI before ligation to pRO12 to form pSAL 5200-6.

Figure 4:
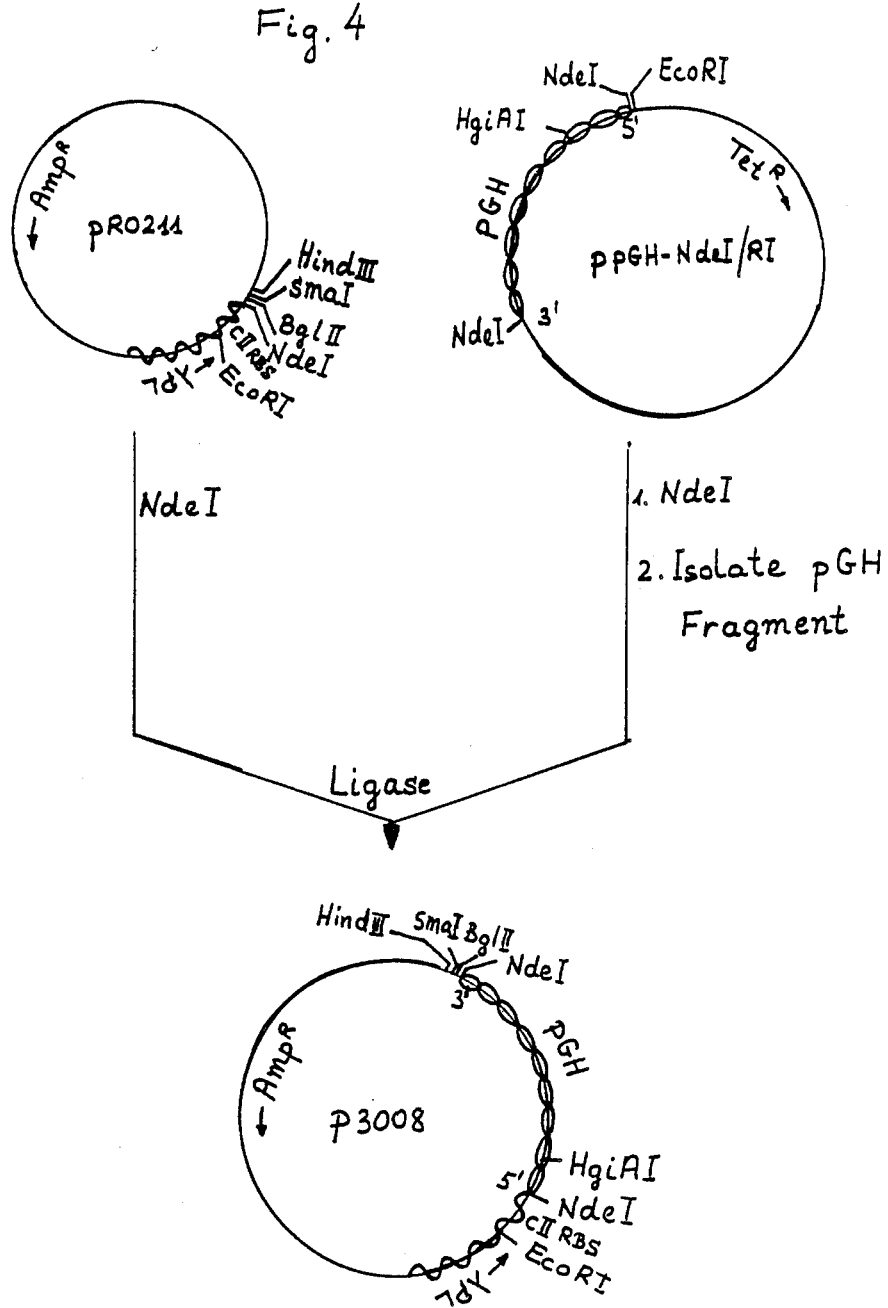

FIG. 4. Construction of p3008.

p3008 (ATCC No. 39804) was constructed by ligating NdeI-digested pRO211 (FIG. 2) with the pGH fragment isolated from an NdeI digest of the plasmid ppGH-NdeI/RI.

ppGH-NdeI/RI contains full length pGH cDNA to both ends of which NdeI sites have been added by means of synthetic linkers.

Figure 5:
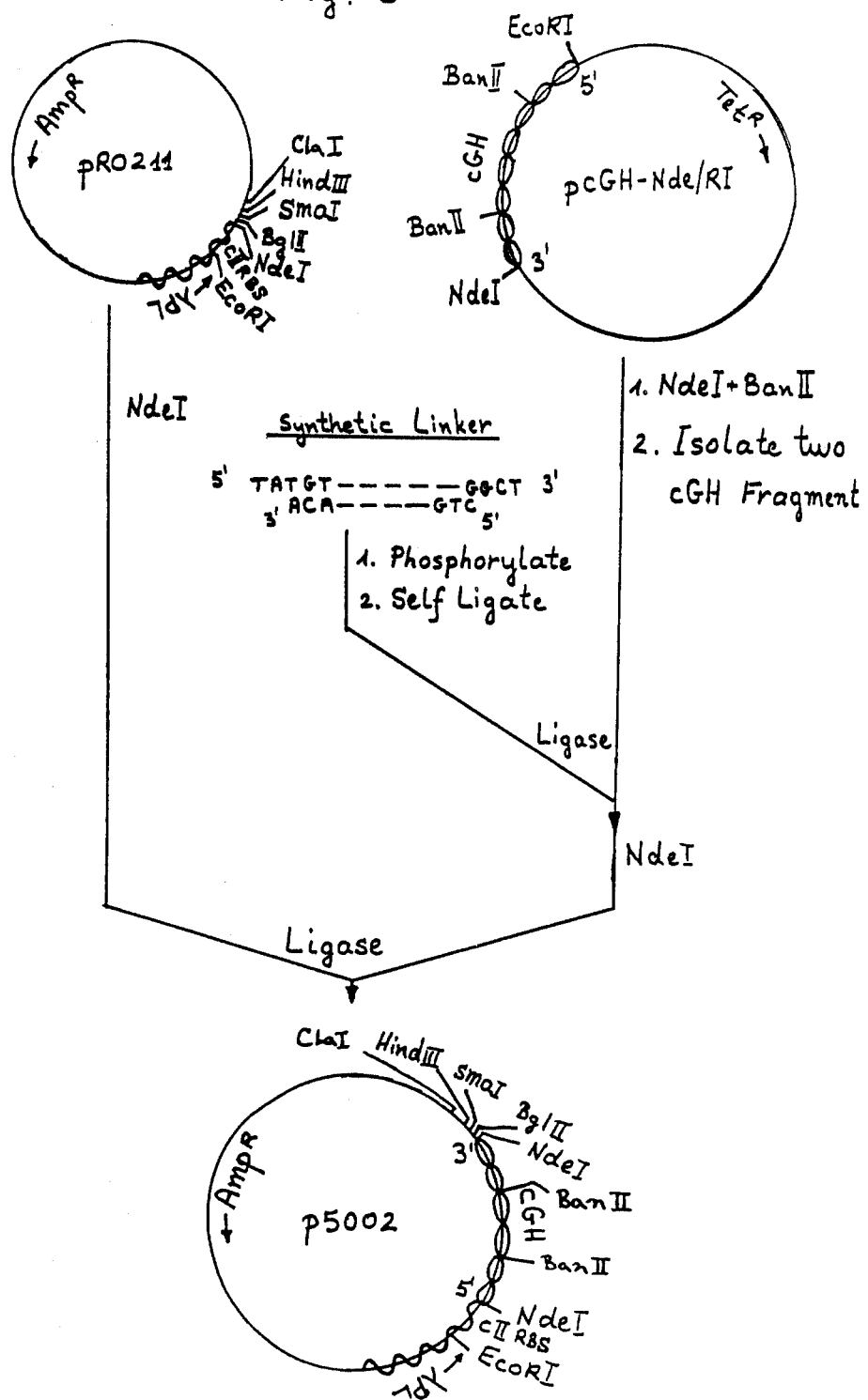

FIG. 5. Construction of p5002.

p5002 was constructed by tripartite ligation of a dimerized synthetic linker and the 2 cGH fragments isolated from an NdeI and BanII digest of the plasmid pcGH-NdeI/RI. The ligation mixture was digested with NdeI and then ligated to the expression vector pRO211 (FIG. 2) after it had been restricted with NdeI. A colony containing the plasmid p5002 was isolated.

The synthetic linker was constructed from two single-stranded synthetic DNAs of the sequence:

```
TATGTTCCCTGCCATGCCCCTCTCCAACCTGTTTGCCAACGCTGTGCTGAGGGCT
    ACAAGGGACGGTACGGGGAGAGGTTGGACAAACGGTTGCGACACGACTC
```

The linker was phosphorylated before ligation. The linker codes for the first 18 amino acids of the N-terminus of the authentic cGH.

The plasmid pcGH-NdeI/RI contains full length cGH cDNA at the 5' end of which there is an EcoRI restriction site and at the 3' end of which there is an NdeI restriction site. These restriction sites were added by means of synthetic linkers.

Figure 6:
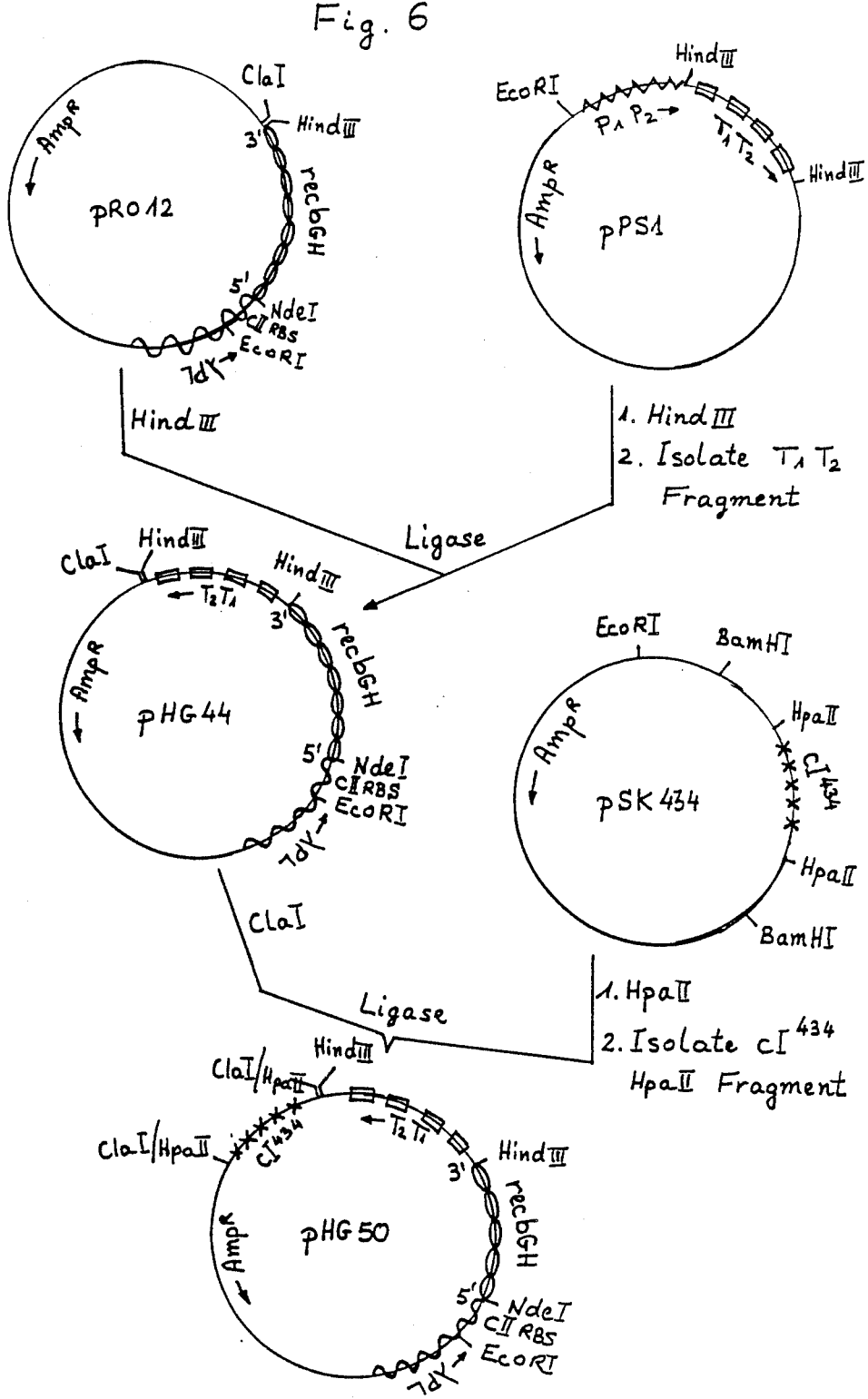

FIG. 6. Construction of pHG44 and pHG50.

pRO12 (FIG. 2) was digested with HindIII. The linear form DNA (form III) was purified from agarose gel and ligated to a HindIII-HindIII fragment of about 1200 base pairs which contains the rRNA operon transcription termination sequences $T_1T_2$. The $T_1T_2$ HindIII-HindIII fragment was isolated from plasmid pPS1 (ATCC No. 39807) which had been digested with HindIII. The resulting plasmid pHG44 (ATCC No. 39806) contains the $T_1T_2$ sequences at the 3' end of the recombinant (rec) bGH sequence.

The plasmid pSK434 (ATCC No. 39784) containing the $\lambda cI^{434}$ repressor sequences was digested with HpaII. The $\lambda cI^{434}$ HpaII-HpaII fragment was isolated and ligated to pHG44 which had been digested with ClaI. The resulting plasmid pHG50 (ATCC No. 39805) contains the $T_1T_2$ transcription termination sequences and the $\lambda cI^{434}$ repressor sequence.

Figure 7:
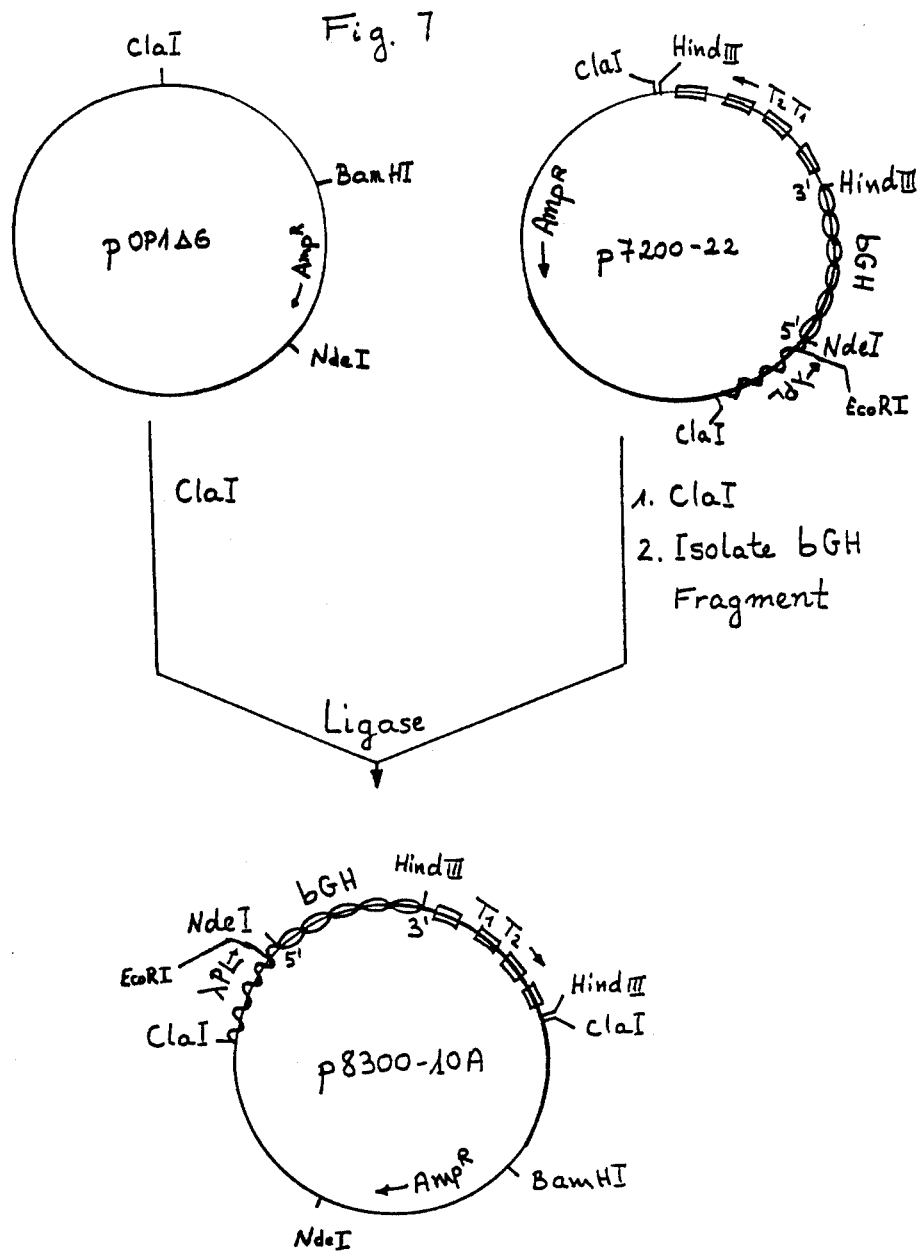

FIG. 7. Construction of p8300-10A.

The plasmid p8300-10A (ATCC No. 39785) which expresses an analog of the natural phenylalanine form of bGH having methionine at the N-terminus (met-phe bGH) was prepared as follows. The plasmid p7200-22 contains the $\lambda P_L$ promoter and ribosomal binding site derived from pJH200 (ATCC No. 39783), DNA encoding met-phe bGH and the $T_1T_2$ rRNA termination sequences. The ClaI-ClaI fragment containing the $\lambda P_L$ promoter, the $C_{II}$ ribosomal binding site, the met-phe bGH gene and the $T_1T_2$ transcription termination sequences was inserted into the unique ClaI site of plasmid pOP1Δ6, a constitutive high copy number plasmid, to form p8300-10A.

Figure 8:
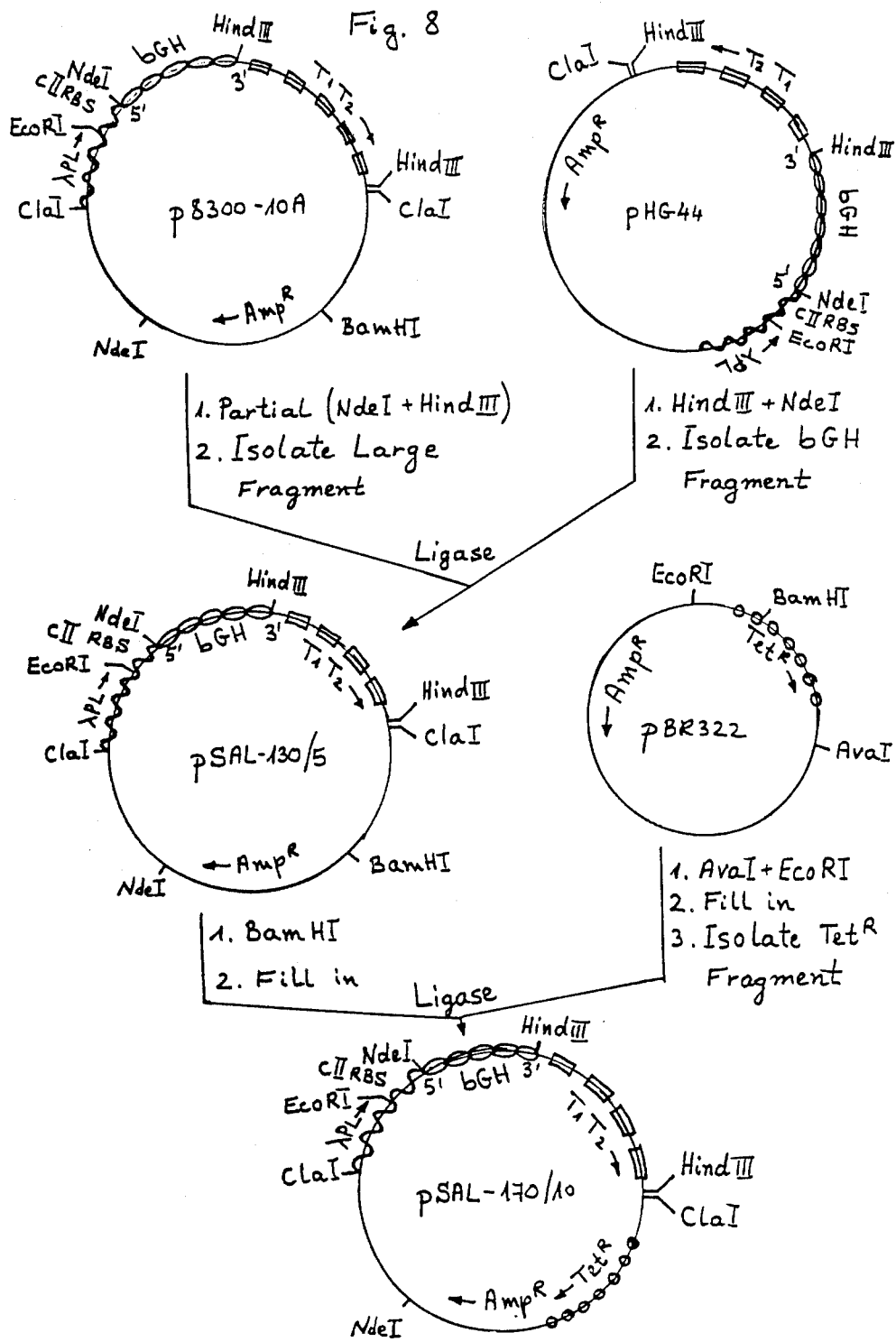

FIG. 8. Construction of pSAL-130/5 and pSAL-170/10.

The plasmid pHG44 (ATCC No. 39806) expressing met-asp-gln bGH protein was digested with NdeI and HindIII. The resulting NdeI-HindIII bGH fragment was isolated and ligated to a fragment from p8300-10A (ATCC No. 39785) prepared by partial digestion with both NdeI and HindIII. Such a ligation replaces the met-phe bGH gene fragment with the met-asp-gln bGH gene fragment. The plasmid so obtained, pSAL-130/5, expresses rec bGH. pSAL-170/10 was obtained by treating the EcoRI-AvaI fragment containing the $Tet^R$ gene of pBR322 plasmid (ATCC No. 37017) with DNA polymerase I (Klenow) and inserting it into pSAL-130/5 which had been digested with BamHI and filled in with DNA polymerase I (klenow).

Figure 9:
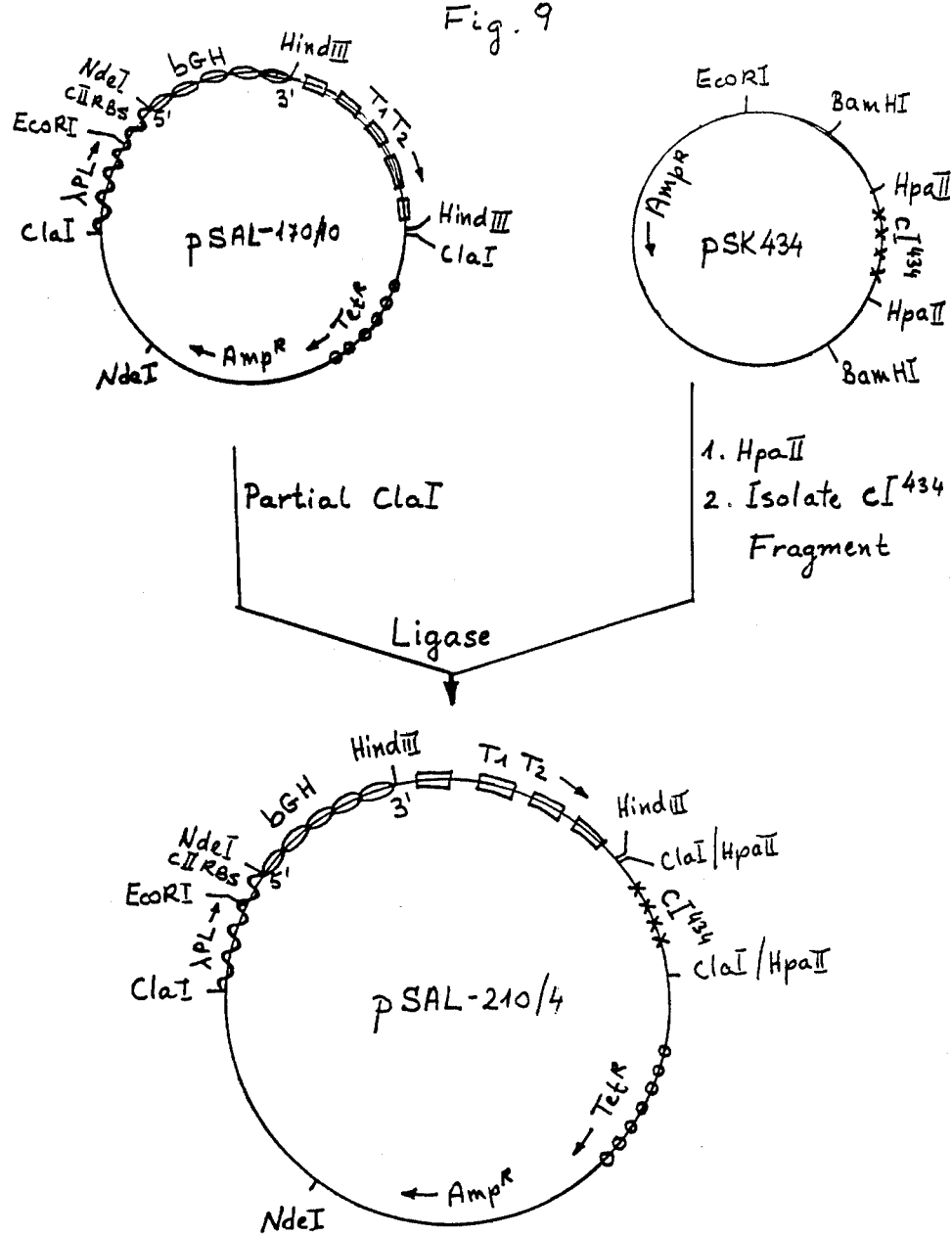

FIG. 9. Construction of pSAL-210/4.

Linear form DNA (form III) was prepared by partial ClaI digestion of pSAL-170/10. It was purified from an agarose gel and ligated to a HpaII-HpaII $cI^{434}$ gene fragment which was isolated from a HpaII digest of the plasmid pSK434 (ATCC No. 39784).

Figure 10:
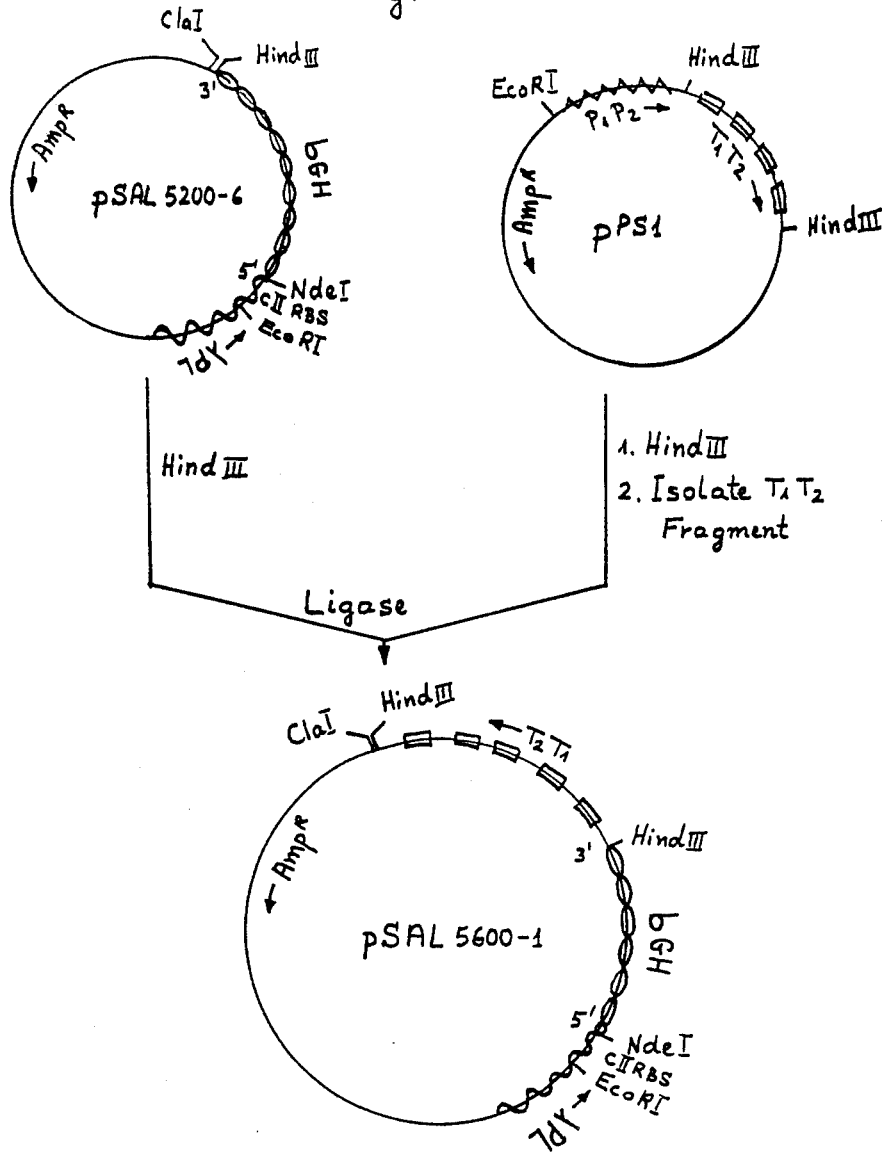

FIG. 10. Construction of pSAL 5600-1.

pSAL 5200-6 (FIG. 3) was digested with HindIII. The linear form DNA (form III) was purified from an agarose gel and ligated to a HindIII-HindIII fragment of about 1200 base pairs which contains the rRNA operon transcription termination sequences, $T_1T_2$. The $T_1T_2$ HindIII-HindIII fragment was isolated from the plasmid pPS1 (ATCC No. 39807) which was digested with HindIII. The resulting plasmid pSAL 5600-1 contains the $T_1T_2$ sequences at the 3' end of the met-asp-gln bGH sequence.

Figure 11:
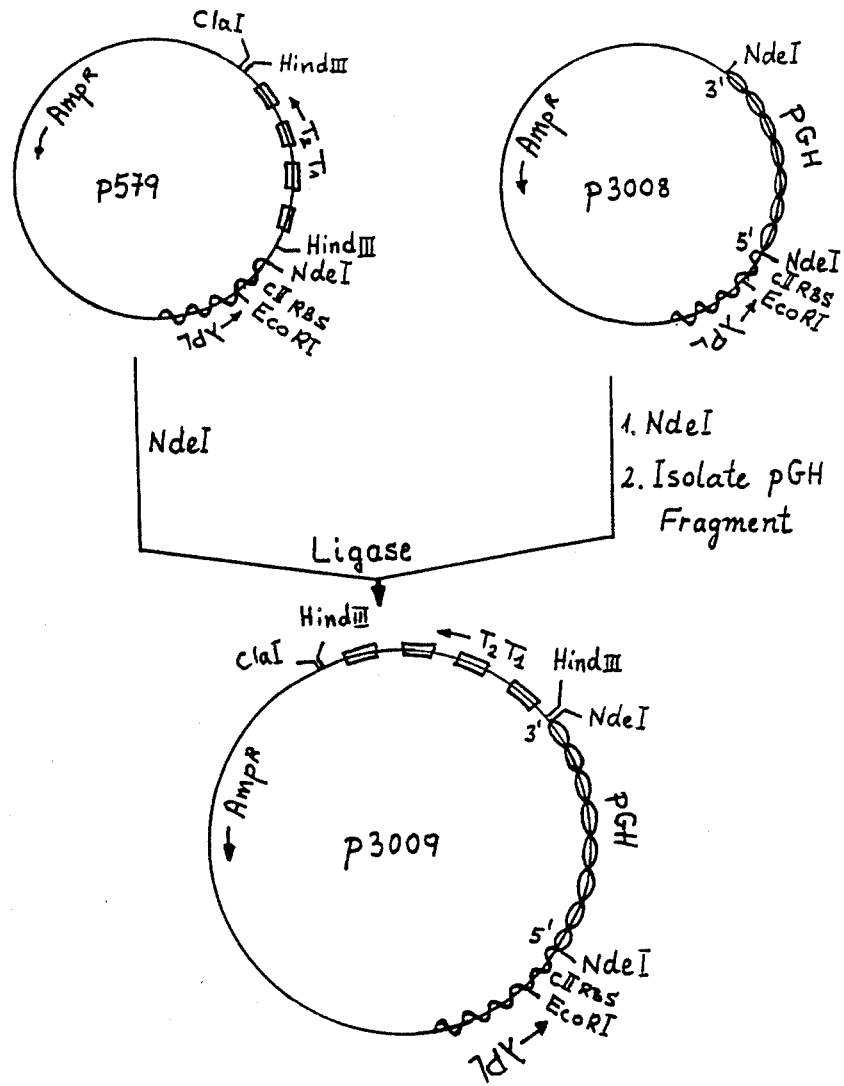

FIG. 11. Construction of p3009.

The NdeI-NdeI pGH fragment was isolated from plasmid p3008 (ATCC No. 39804) (FIG. 5). The fragment was inserted into the unique NdeI site of the expression vector p579 (FIG. 19) which had been digested with NdeI. The resulting plasmid p3009 expresses an analog of natural porcine growth hormone protein having a methionine residue added at the N-terminus.

Figure 12:
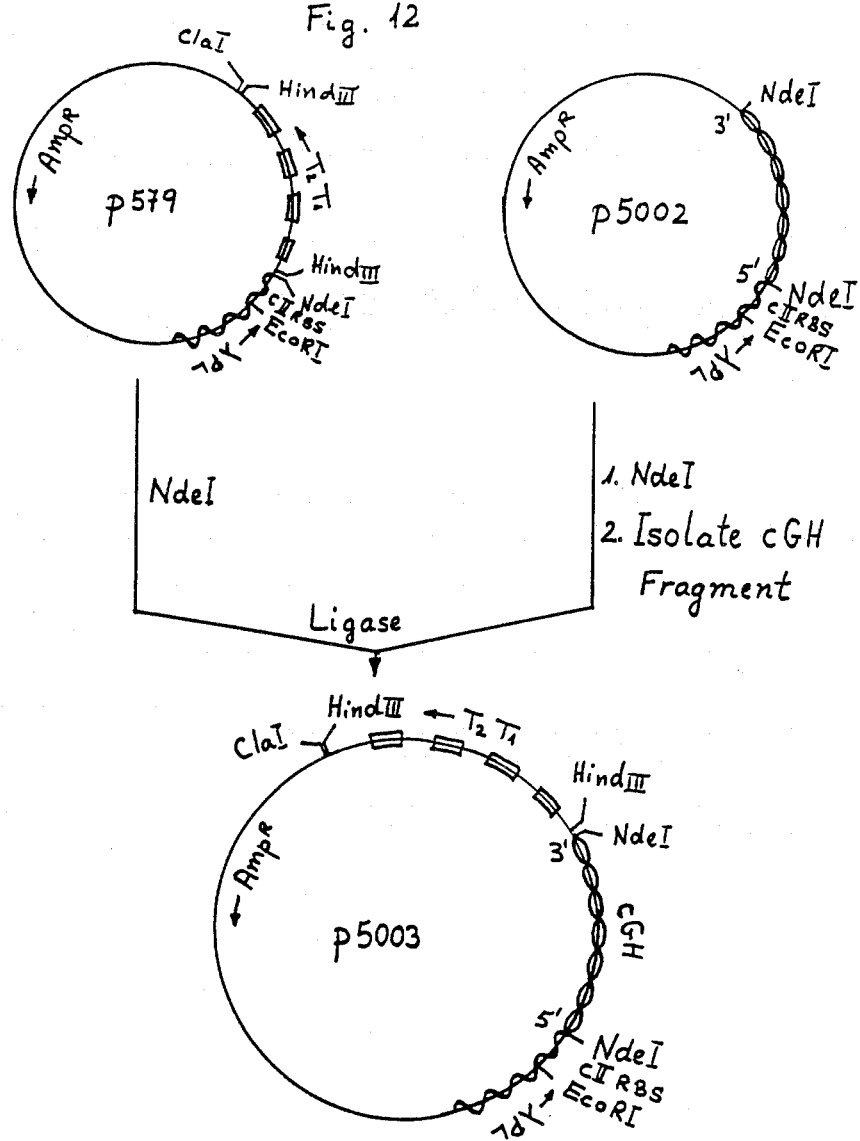

FIG. 12. Construction of p5003.

The NdeI-NdeI cGH fragment was isolated from plasmid p5002. The fragment was inserted into the unique NdeI site of the expression vector p579 (FIG. 19) which had been digested with NdeI. The resulting plasmid p5003 (ATCC No. 39792) expresses an analog of natural chicken growth hormone protein having a methionine residue added at the N-terminus.

Figure 13:
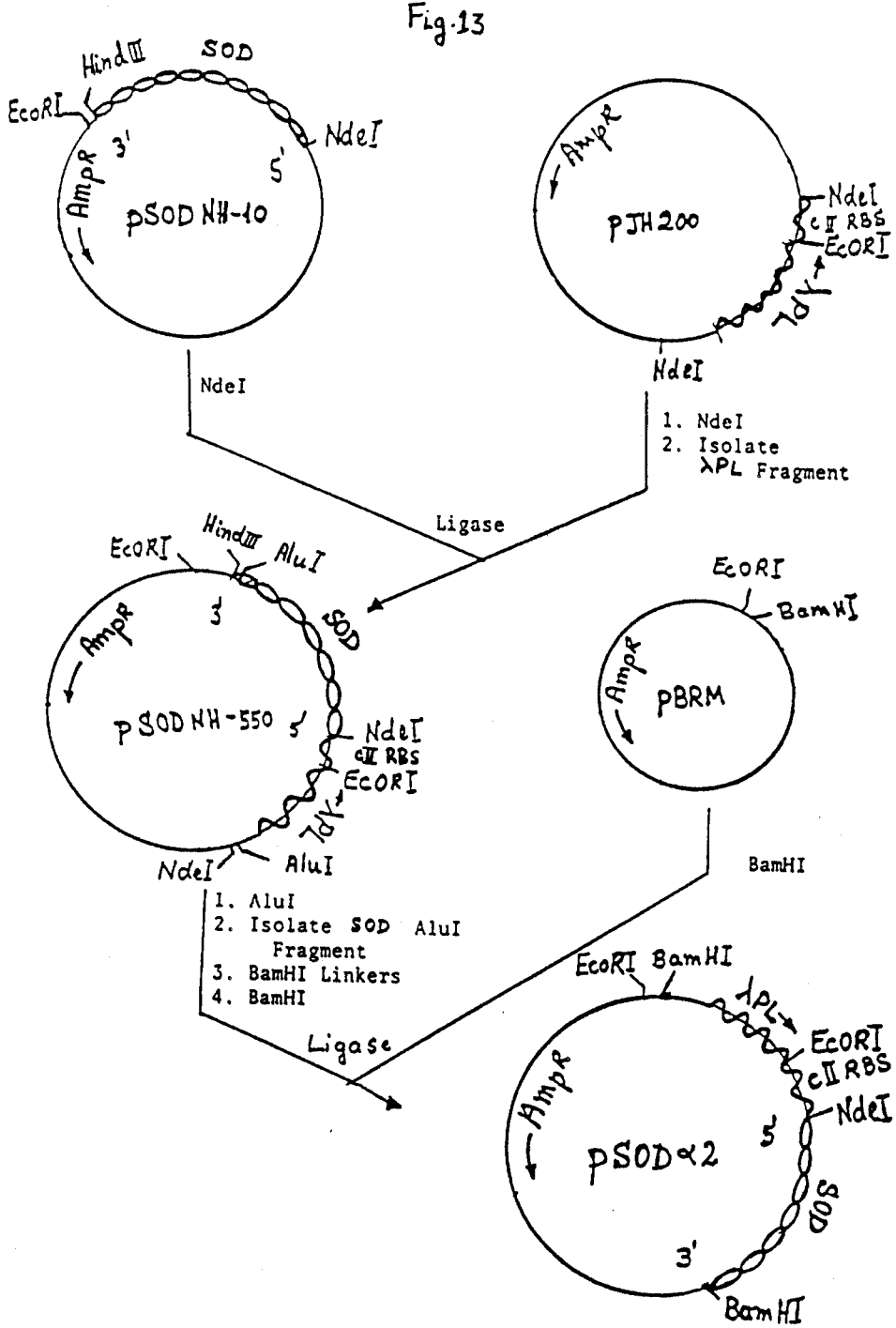

FIG. 13. Construction of pSODα2.

The pJH200 (ATCC No. 39783) expression vector was digested with NdeI. The 550 base pair NdeI fragment containing the $\lambda P_L$ promoter and $C_{II}$ ribosomal binding site was isolated and inserted into the unique NdeI site of plasmid pSOD NH-10 which had been digested with NdeI. (Plasmid pSOD NH-10 is derived from a cDNA clone of human SOD [Lieman-Hurwitz, J., et al., PNAS (1982) 79: 2808]) The resulting plasmid pSOD NH-550 was digested with AluI. (Only the relevant AluI site is shown in the figure.) The large AluI fragment containing the $\lambda P_L$ promoter and the SOD gene was isolated. BamHI linkers were attached and the resulting fragment was digested with BamHI. The BamHI digestion product was inserted into the unique BamHI site of pBRM (ATCC No. 37283) to form pSODα2 (ATCC No. 39786).

Figure 14:
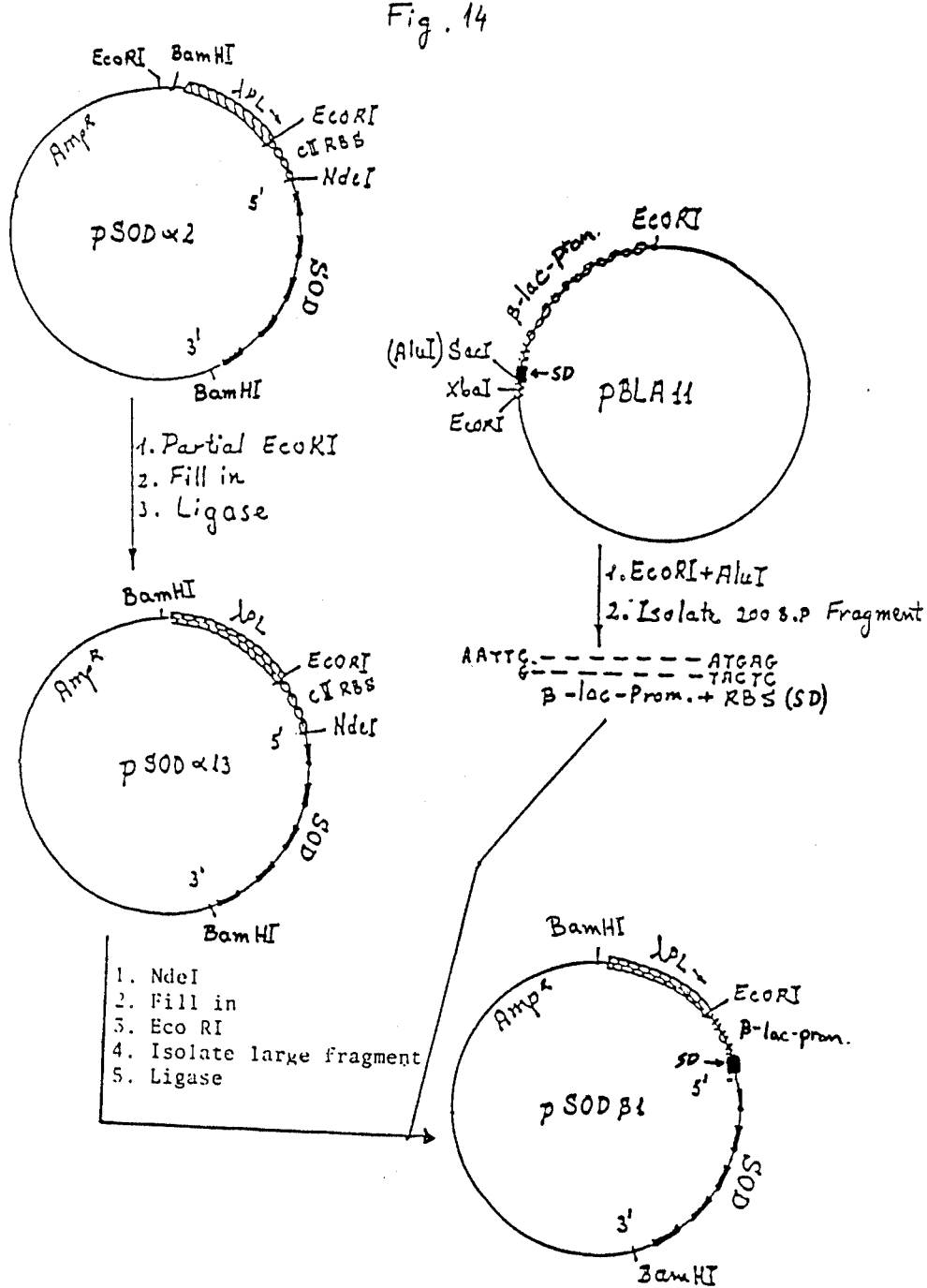

FIG. 14. Construction of pSODα13 and pSODβ1.

The plasmid pSODα2 (ATCC No. 39786) was partially digested with EcoRI and the resulting linear form DNA was isolated from an agarose gel. The purified DNA was filled in with DNA polymerase I (Klenow) and religated. The resulting clone pSODα13 contains one EcoRI site located at the 5' end of the ribosomal binding site. A fragment containing the β-lactamase promoter and ribosomal binding site was isolated from plasmid pBLA11 (ATCC No. 39788) which had been digested with EcoRI and AluI. The 200 base pair fragment was ligated to the large fragment isolated from pSODα13 which had been digested with NdeI, filled in with DNA polymerase I (Klenow) and then digested with EcoRI. The resulting plasmid pSODβ1 contains the ribosomal binding site of the β-lactamase gene and the $\lambda P_L$ promoter.

Figure 15:
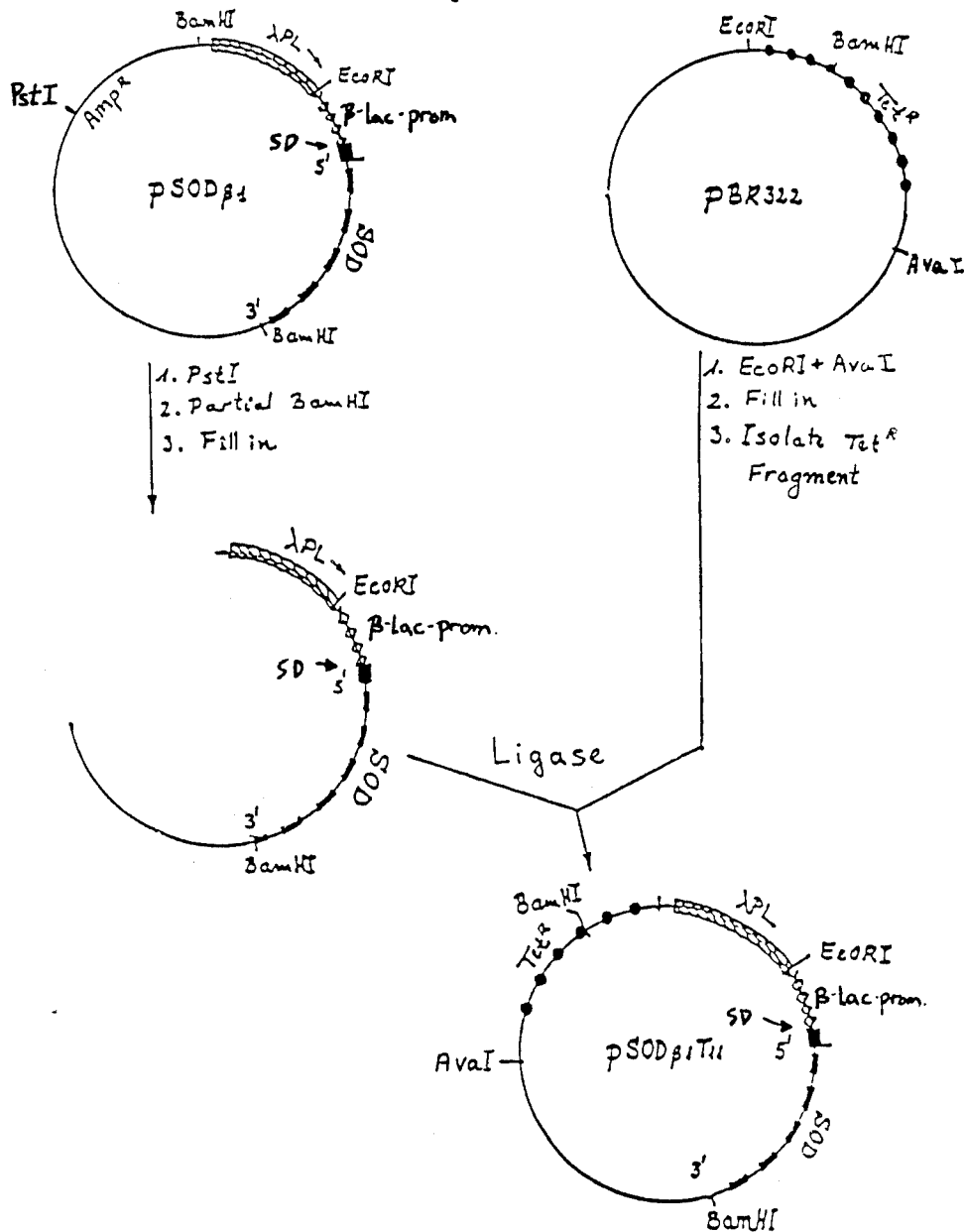

FIG. 15. Construction of pSODβ$_1$T$_{11}$.

Plasmid pBR322 (ATCC No. 37017) was digested with EcoRI and AvaI. The resulting DNA was filled in with DNA polymerase I (Klenow). The $Tet^R$ gene fragment was then isolated and ligated to the large fragment isolated from pSODβ1 (FIG. 14) plasmid which had been digested with PstI followed by a partial BamHI digest and then filled in with DNA polymerase I (Klenow). The resulting plasmid pSODβ$_1$T$_{11}$ contains the $Tet^R$ gene.

FIG. 16. Construction of pSODβ$_1$TT-1.

The rRNA $T_1T_2$ transcription termination fragment was isolated from plasmid pPS1 (ATCC No. 39807) which had been digested with HindIII and filled in with DNA polymerase I (Klenow). The fragment was ligated to plasmid pSODβ$_1$T$_{11}$ (FIG. 15) which had been partially digested with BamHI and filled in with DNA Polymerase I (Klenow).

Figure 17:
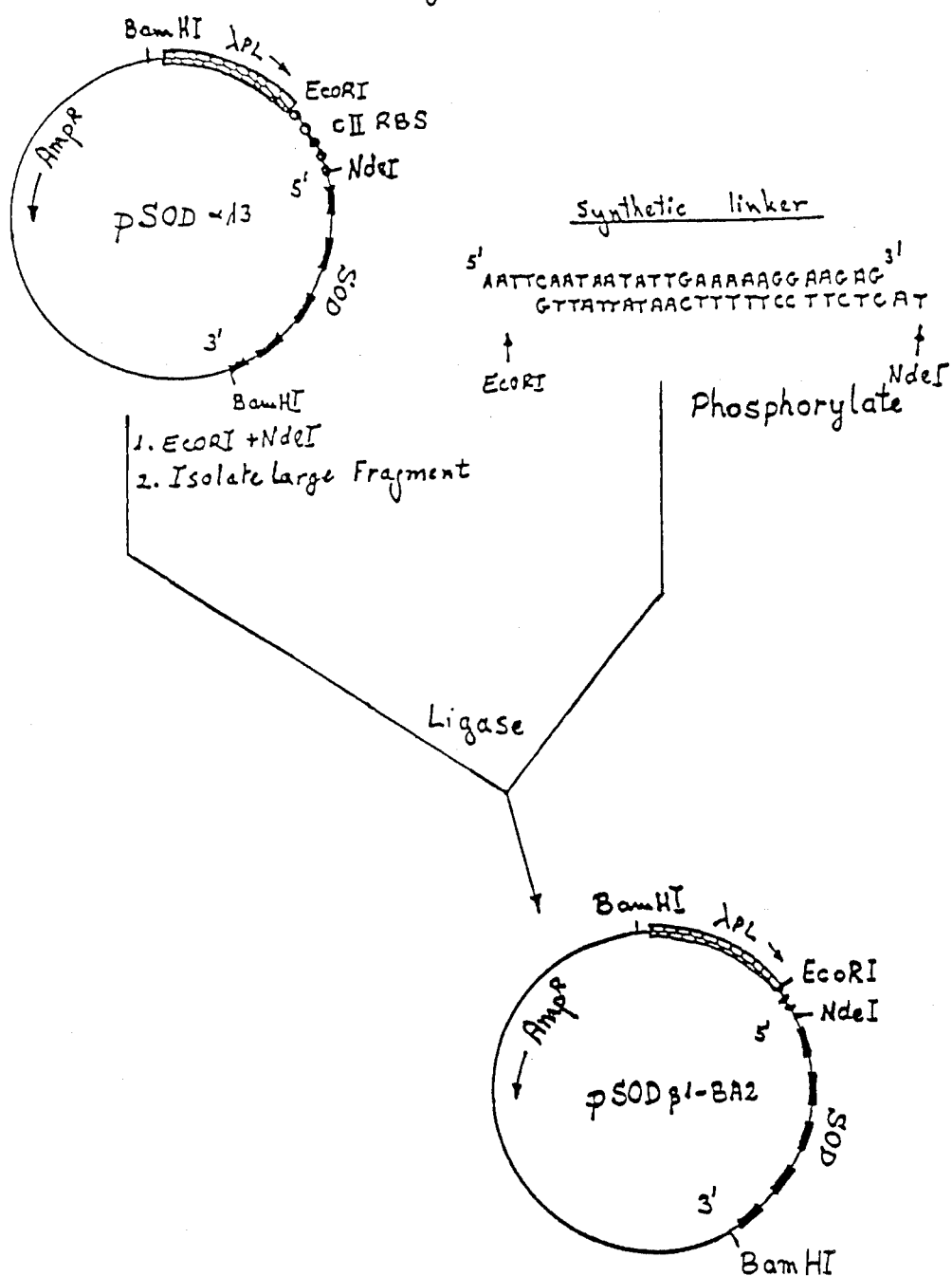

FIG. 17. Construction of pSODβ$_1$-BA2.

A synthetic DNA fragment with the sequence:

```
5'-AATTCAATAATATTGAAAAAGGAAGAG—3'
     GTTATTATAACTTTTTCCTTCTCAT
``` which is similar to the sequence of the natural β-lactamase ribosomal binding site, was phosphorylated and ligated to the large fragment of pSODα13 plasmid (FIG. 14) which had been digested with NdeI and EcoRI.

Figure 18:
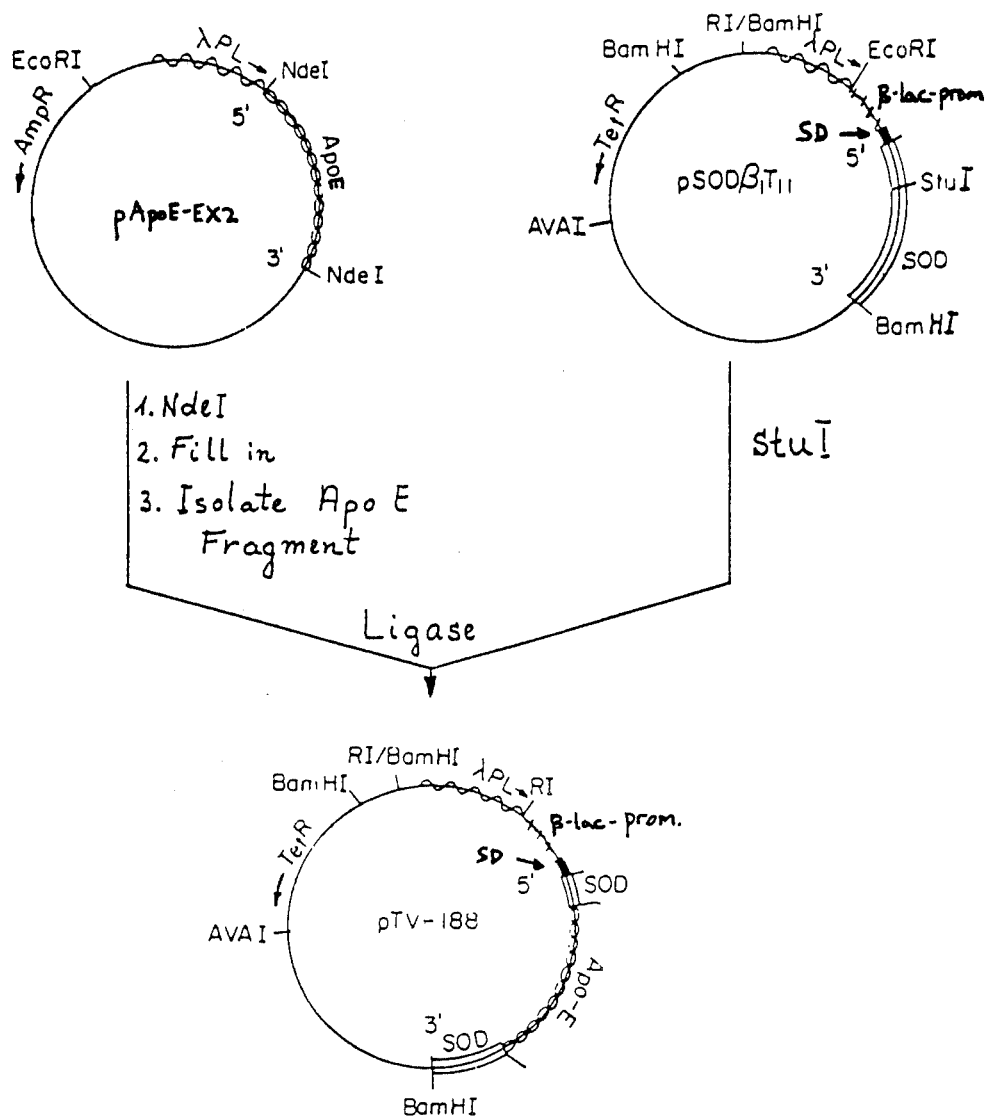

FIG. 18. Construction of pTV-188.

Plasmid pApoE-EX2 (ATCC No. 39787) was digested with NdeI and then fragments filled in with DNA polymerase I (Klenow). The resulting ApoE gene fragment was isolated and inserted into the unique blunt end StuI site of the pSODβ$_1$T$_{11}$ plasmid (FIG. 15). The resulting plasmid pTV-188 expresses an ApoE fused protein.

Figure 19:
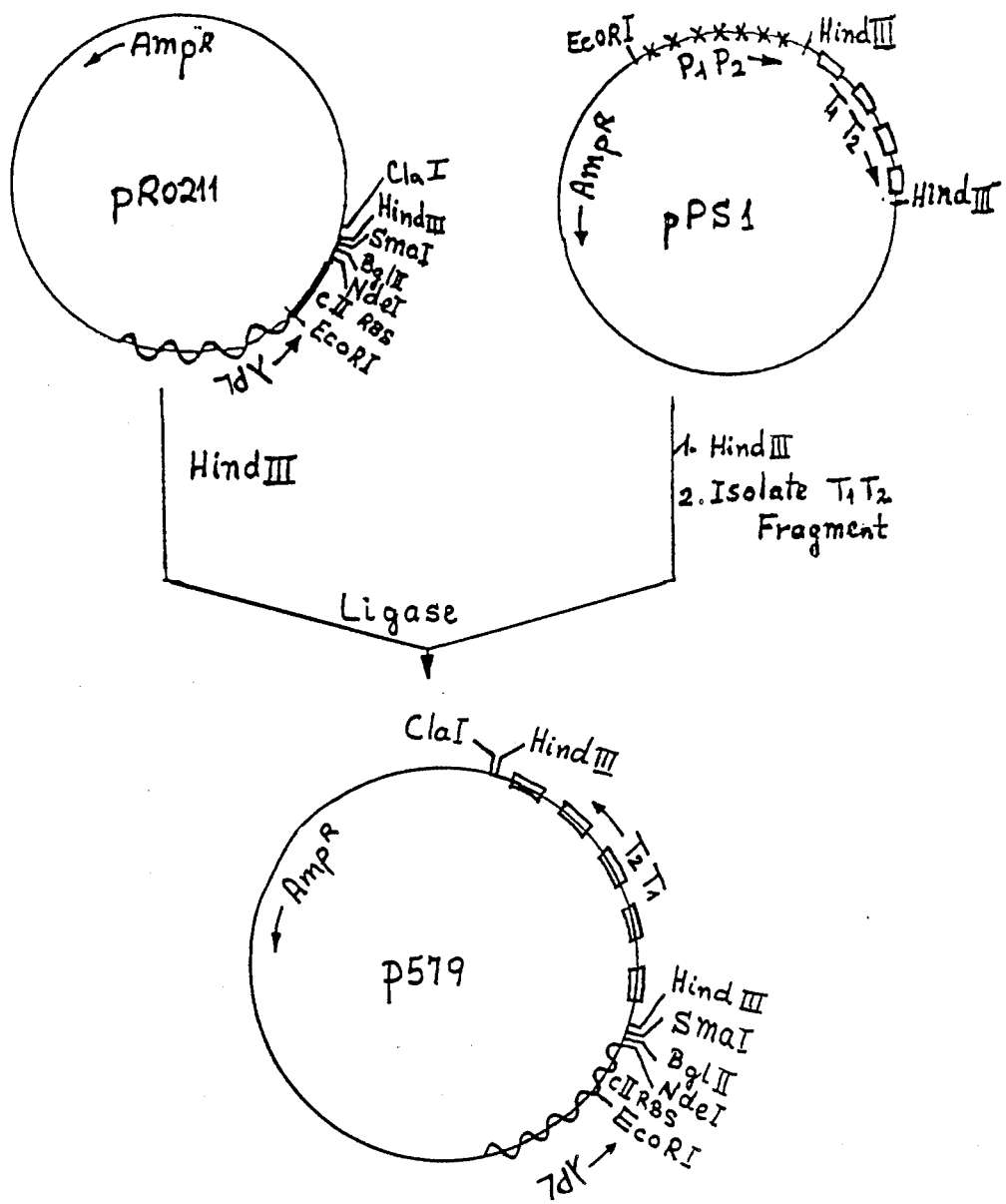

FIG. 19. Construction of p579.

The rRNA operon T$_1$T$_2$ transcription termination fragment was isolated from plasmid pPS1 (ATCC No. 39807) which had been digested with HindIII. The T$_1$T$_2$ fragment was inserted into the unique HindIII site of pRO211 (FIG. 2) which had been digested with HindIII. The resulting expression vector, p579, contains the λP$_L$ promoter, the C$_{II}$ ribosomal binding site, followed by the T$_1$T$_2$ transcription termination signals.

Figure 20:
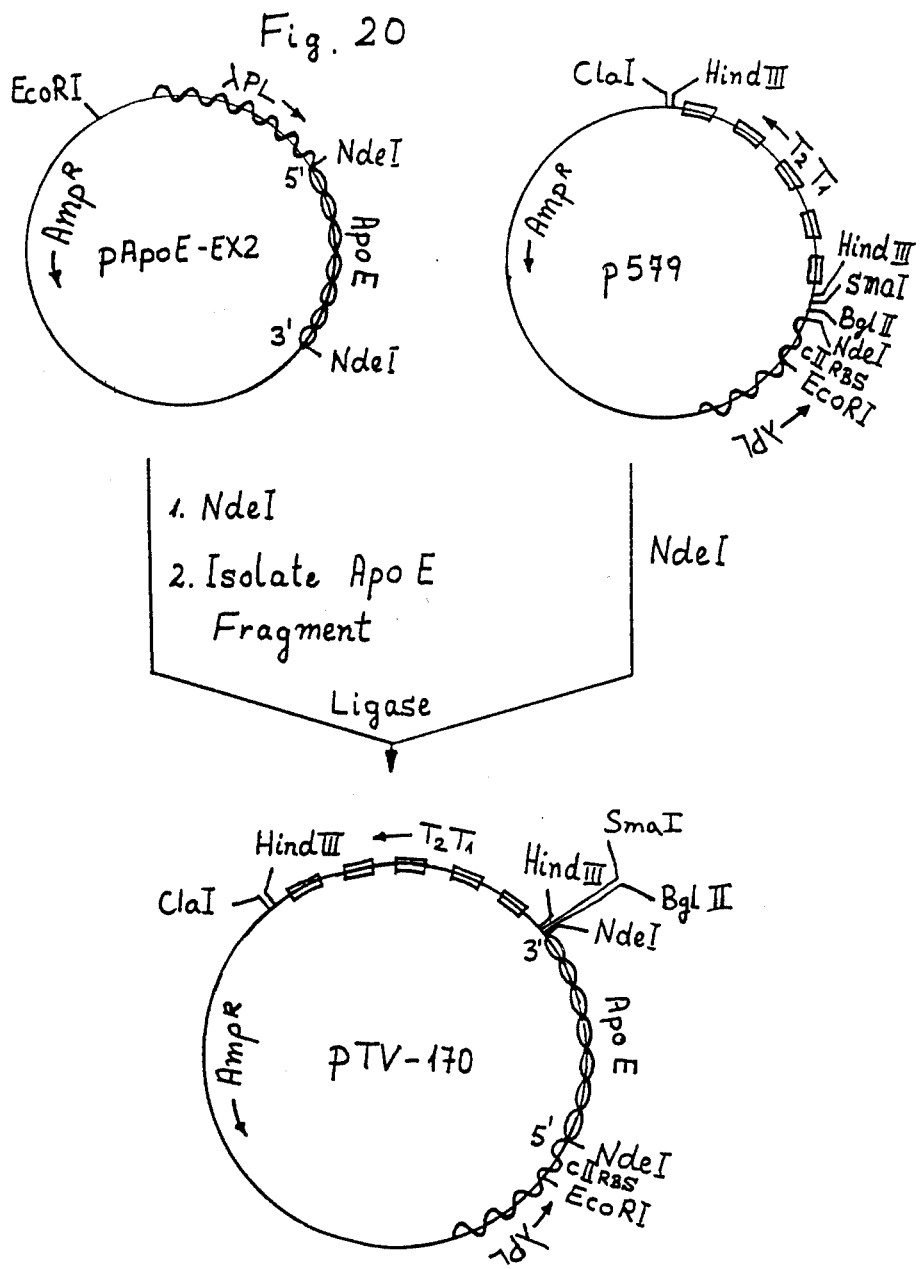

FIG. 20. Construction of pTV-170.

The NdeI-NdeI ApoE fragment was isolated from plasmid pApoE-EX2 (ATCC No. 39787) and inserted into the unique NdeI site of the expression vector p579 (FIG. 19) which had been digested with NdeI. The resulting plasmid pTV-170 expresses an analog of natural human ApoE protein having a methionine residue added at the N-terminus.

FIG. 21. Construction of pTV-190.

The plasmid pTV-170 (FIG. 20) was partially digested with NdeI and filled in with DNA Polymerase I (Klenow). The isolated linear form DNA was religated to yield the plasmid pTV-190 which was analyzed and found to have only one NdeI site at the 5' end of the ApoE gene.

FIG. 22. Construction of pTV-194.

The β-lactamase promoter and ribosomal binding site fragment was isolated from plasmid pBLA11 (ATCC No. 39788) after digestion with EcoRI and AluI. This fragment was ligated to the large fragment of pTV-170 (FIG. 20) plasmid which had been digested with NdeI, filled in with DNA polymerase I (Klenow) and then digested with EcoRI.

Figure 23:
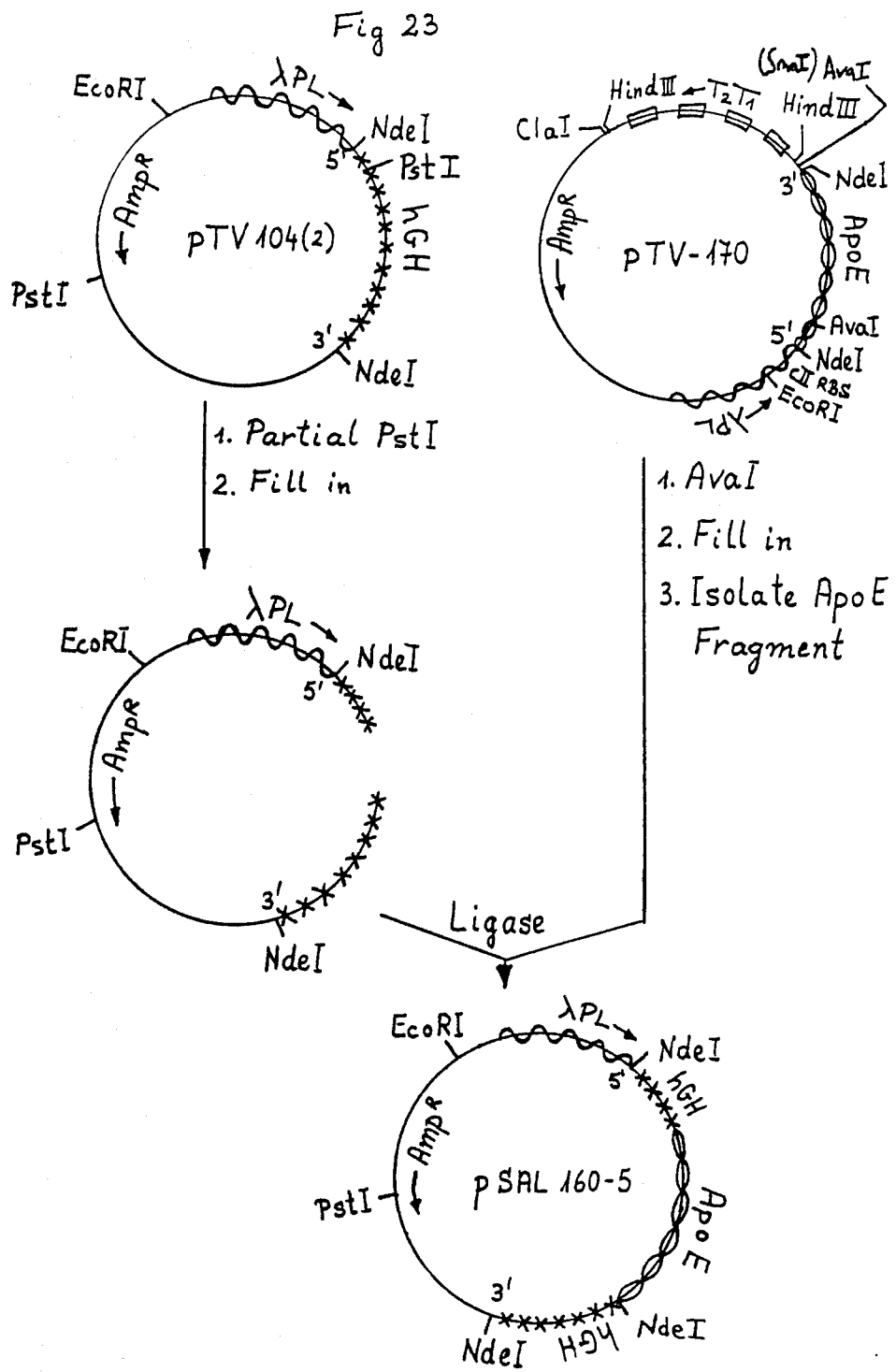

FIG. 23. Construction of pSAL 160-5.

An AvaI-AvaI fragment containing the ApoE DNA sequence was isolated from pTV-170 (FIG. 21) which was digested with AvaI. The fragment was filled in with DNA polymerase I (Klenow) and isolated on agarose gel. The purified ApoE fragment was inserted into the PstI site of the pTV 104(2) plasmid (ATCC No. 39384) which was partially digested with PstI and filled in with DNA Polymerase I (Klenow). The resulting plasmid is designated pSAL 160-5.

Figure 24:
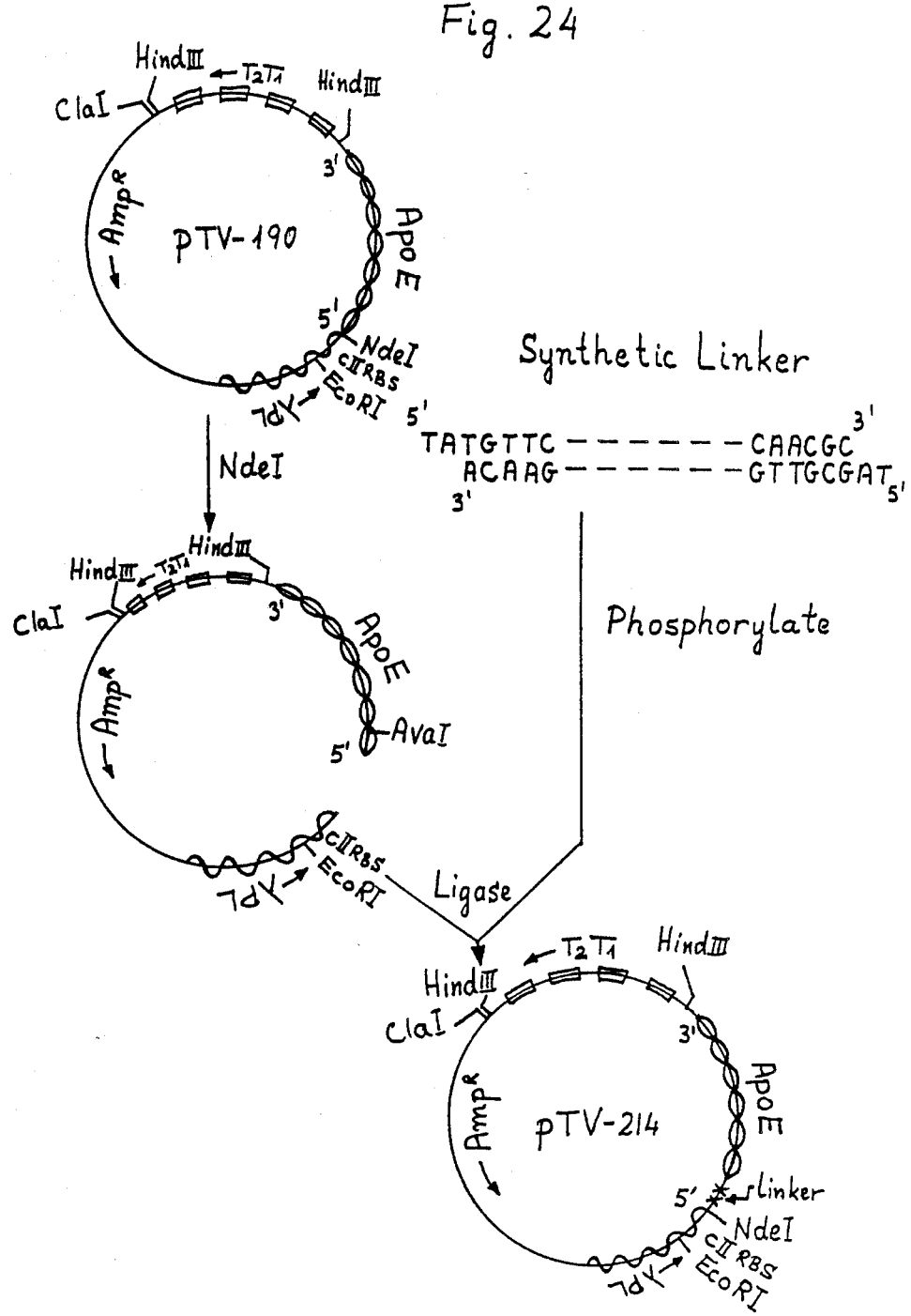

FIG. 24. Construction of pTV-214.

A synthetic fragment containing the first 14 amino acids of human growth hormone with the sequence:

TATGTTCCCAACCATTCCATTATCCCGTCTGTTCGACAACGC
 ACAAGGGTTGGTAAGGTAATAGGGCAGACAAGCTGTTGCGAT was phosphorlylated using γ-$^{32}$P-ATP and polynucleotide kinase. The phosphorylated linker was inserted into the unique NdeI site of pTV-190 plasmid which had been digested with NdeI.

DETAILED DESCRIPTION OF THE INVENTION

A method of producing enzymatically active eucaryotic superoxide dismutase (SOD) or an analog thereof in a bacterial cell has been discovered. The bacterial cell contains and is capable of expressing a DNA sequence encoding the superoxide dismutase or analog. The method comprises maintaining the bacterial cell under suitable conditions and in a suitable production medium. The production medium is supplemented with an amount of Cu$^{++}$ so that the concentration of Cu$^{++}$ in the medium is greater than about 2 ppm.

The bacterial cell can be any bacterium in which a DNA sequence encoding eucaryotic superoxide dismutase has been introduced by recombinant DNA techniques. The bacterium must be capable of expressing the DNA sequence and producing the protein product. The suitable conditions and production medium will vary according to the species and strain of bacterium.

The bacterial cell may contain the DNA sequence encoding the superoxide dismutase or analog in the body of a vector DNA molecule such as a plasmid. The vecotr or plasmid is constructed by recombinant DNA techniques to have the sequence encoding the SOD incorporated at a suitable position in the molecule.

In a preferred embodiment of the invention the bacterial cell is an *Escherichia coli* cell. The preferred strain of *E. coli* is strain A1645. The *E. coli* cell of this invention contains a plasmid which encodes for the SOD or its analog. In a preferred embodiment of the invention the SOD is human superoxide dismutase or an analog thereof.

The preferred embodiments of the invention concern *E. coli* strains which contain the plasmids pSODβ$_1$, pSODα2, pSODβT11, pSODβ$_1$-BA2 or pSODβ$_1$TT1. Methods of constructing these plasmids are described in the Description of the Figures and the plasmids themselves are described in Example I. These plasmids can be constructed from available starting materials by persons of ordinary skill in the art. *E. Coli* strains containing the various plasmids which are useful in constructing plasmids encoding eucaryotic superoxide dismutase have been deposited with the American Type Culture Collection, Rockville, Md. 20852, pursuant to the provisions of the Budapest Treaty of the International Recognition of the Deposit of Microorganisms for the purposes of Patent Procedure. These plasmids and their accession numbers are: pBRM ATCC 37283; pSODα2 ATCC 39786; pBR322 ATCC 37017; pBLA11 ATCC 39788; pJH 200 ATCC 39783 and pPSI ATCC 39807.

In a specific embodiment of the invention an enzymatically active human superoxide dismutase analog is produced by an *E. coli* strain A2097 cell containing the plasmid pSODα2. This cell has been deposited with the American Type Culture Collection under accession number ATCC 39786.

The suitable production medium for the bacterial cell can be any type of acceptable growth medium such as casein hydroysate or LB (Luria Broth) medium. Suitable growth conditions will vary with the strain of *E. coli* and the plasmid it contains, for example *E. coli* A1645 containing plasmid pSODβ$_1$T11 are induced at 42° C. and maintained at that temperature from about 1 to about 5 hours. The suitable conditions of temperature, time, agitation and aeration for growing the inoculum and for growing the culture to a desired density before the production phase as well as for maintaining the culture in the production period are described in Example 2.

The concentrations of $Cu^{++}$ ion in the medium that is necessary to produce enzymatically active SOD will vary with the type of medium used. In a casein hydrolysate medium the $Cu^{++}$ ion concentration of 200 ppm has been found effective.

In a LB medium a $Cu^{++}$ concentration of 75 ppm has been found effective. It is preferred that in all complex types of growth mediums the concentration of $Cu^{++}$ in the medium is from about 50 to about 250 ppm.

Most eucaryotic superoxide dismuatses are Cu/Zn metalloproteins. In a specific embodiment of the invention $Zn^{++}$ is added as a supplement to the medium, so that the concentration of $Zn^{++}$ in the medium is greater than about 2 ppm. In a preferred embodiment of the invention $Cu^{++}$ and $Zn^{++}$ concentrations are supplemented by adding 0.8 g/l of $CuSO_4.5H_2O$ and 10 mg./l of $ZnSo_4.7H_2O$.

The specific ingredients of the suitable stock, culture, inoculating and production mediums may vary and are known to those of ordinary skill in the art. Specific examples of suitable mediums are described in Example 2.

The invention also concerns a method of recovering purified enzymatically active eucaryotic SOD or an analog thereof produced in a bacterial cell in accordance with the methods of this invention.

The bacterial cell is first isolated from the production medium after the culture has been chilled. The cell may be isolated by any nondisruptive method such as centrifugation or filtration. The cell is then suspended in a suitable solution having a pH from about 7.0 to about 8.0. It is preferred that a 50 mM sodium phosphate solution of a pH of about 7.8 be used. The cell wall is disrupted by a suitable means such as a blender or a cell disrupter and the resulting homogeneous suspension is sonicated under suitable conditions. The sonication may be by means of a continuous flow cell. The resulting sonicated solution is then centrifuged under suitable conditions so as to separate the cell debris from the protein supernatant solution.

The supernatant is then heated for about 2 hours at about 65° C., cooled and centrifuged under the same conditions as were used in the previous centrifugation step in order to result in a clear protein solution as a supernatant. The supernatant is then concentrated to an appropriate volume, e.g. concentrated to 1 liter in an ultrafiltration device using a 10,000 molecular weight cutoff.

The concentrated protein solution is then subjected to ion exchange chromatography on a suitable anion exchanger equilibrated at a pH from about 7.0 to about 8.0. If is preferred that the chromatography should be carried out on a DEAE-Sephacel column equilibriated with 150 mM sodium phosphate buffer having a pH of about 7.8. The resulting flow through solution containing the superoxide dismutase or analog is then collected, concentrated to an appropriate volume and dialyzed against a buffered solution with a pH from about 7.0 to about 8.0. This can be done in an ultrafiltration device against a 20 mM Tris-HCl solution of a pH of about 7.8.

This concentrated solution is then subjected to ion exchange chromatography on a suitable anion exchanger equilibrated at a pH from about 7.0 to about 8.0. A QAE-Sepharose column equilibrated with 20 mM Tris-HCl having a pH of about 7.8 is suitable. The protein bound to the anion exchanger is subjected to a suitable salt gradient e.g. 0–200 mM NaCl in 20 mM Tris HCl pH 7.8. The resulting fractions containing the SOD or analog are collected, concentrated e.g. with an ultrafiltration device, dialyzed against distilled water and adjusted to a pH from about 4.0 to about 5.0 with a suitable buffer. In a preferred embodiment the solution of interest is brought to 100 mM Sodium Acetate by adding 1M Sodium Acetate having a pH of about 4.8.

This buffered solution is again subjected to ion exchange chromatography but with a cation exchanger. A CM-Sepharose column equilibrated with a 100 mM sodium acetate buffer having pH of about 4.7 is suitable. The protein bound to the cation exchanger is subjected to a suitable salt gradient, such as 100 to 500 mM NaCl in 100 mM sodium acetate pH 4.7 and the resulting fractions containing the purified SOD or analog are collected.

The fractions containing the purified SOD may be concentrated e.g. by ultrafiltration and lyophilized for storage.

The invention also concerns purified enzymatically active eucaryotic superoxide dismutate or analogs thereof produced and purified by the methods of this invention. The preferred embodiment of this invention concerns purified enzymatically active human superoxide dismutase and analogs thereof prepared and purified by the methods of this invention.

EXAMPLES

The examples which follow are set forth to aid in understanding the invention but are not intended to, and should not be construed as to, limit its scope in any way. The examples do not include detailed descriptions for conventional methods employed in the construction of vectors, the insertion of genes encoding polypeptides of interest into such vectors or the introduction of the resulting plasmids into bacterial hosts. Such methods are well-known to those of ordinary skill in the art and are described in numerous publications including the following:

T. Maniatis, E. F. Fritsch and J. Sambrook, Molecular Cloning; A Laboratory Manual, Cold Spring Harbor Laboratory, NY (1982).

Methods in Enzymology, vol. 65, Nucleic Acids (Part 1), edited by Lawrence Grossman and Kivie Moldave, Academic Press, 1980.

Methods in Enzymology, vol. 68, Recombinant DNA, edited by Ray Wu.

Methods in Enzymology, vol. 100, Recombinant DNA (Part B), edited by Ray Wu, Lawrence Grossman, Kivie Moldave, Academic Press, 1983).

Methods in Enzymology, vol. 101, Recombinant DNA (Part C), edited by Ray Wu, Lawrence Grossman, Kivie Moldave, Academic Press, 1983.

Principles of Gene Manipulation, An Introduction to Genetic Engineering, 2nd Edition, edited by R. W. Old and S. B. Primrose, Univ. of Calif. Press (1981).

H. V. Bernard et al., Gene (1979) 5, 59.

A. B. Oppenheim et al., J. Mol. Biol. (11982) 158, 327.

E. Remaut et al., Gene (1981), 15, 81.

EXAMPLE 1

Human Cu/Zn Superoxide Dismutase (SOD) Expression Plasmids

The starting point for Cu/Zn SOD cDNA modifications is the plasmid pS61-10 which was described in PNAS (1982), 79: 2808. The SOD cDNA found in the plasmid is also referred to in copending U.S. patent application Ser. No. 489,786 filed on Apr. 29, 1983. The SOD cDNA was modified to introduce an NdeI restriction site at the 5' end of the gene and a Hind III restriction site at the 3' end of the gene. The resulting plasmid, pSOD NH-10, contains SOD cDNA bounded by unique restriction sites.

I. pSODα2

The construction of pSODα2 is shown in FIG. 13 and described in the Description of the Figures. To construct pSODα2, the promoter, the NutL and the ribosomal binding site were excised from the expression vector pJH200 and placed in front of the SOD gene of plasmid pSOD NH-10. Then, the fragment containing both the promoter, the RBS and the SOD gene was inserted into the vector pBRM (Hartman et al, PNAS 79: 223-237 (1982).

pSODα2 was introduced into E. coli strain A 2097 by transformation using known methods. The clones obtained produce upon growth and induction an SOD analog protein. The amount of SOD analog produced by pSODα2 was about 0.1-0.3% of the total protein produced by the bacteria as calculated from scanning of Coomasie stained SDS polyacrylamide gels (Table 1). The SOD analog produced is probably identical to that produced by pSODβ1.

II. pSODβ1

The construction of pSODβ1 is shown in FIG. 14 and described in the Description of the Figures. To construct pSODβ1, the cII RBS of pSODα2, was replaced with the β-lactamase promoter and ribosomal binding site derived from pBLA11.

pBLA11 contains the promoter and ribosomal binding site of the β-lactamase gene found in pBR322 between coordinates 4157 and 4353. An EcoRI linker was added upstream of the promoter and a restriction site linker was added immediately after the initiation codon ATG. Thus the sequence of the coding strand beginning with the initiation codon is ATGAGCTCTAGAATTC. pBLA11 was deposited in the American Type Collection Center as ATCC No. 39788.

pSODβ1 was introduced into E. coli strain A1645 by transformation using known methods. The clones obtained produce upon growth and induction an SOD analog.

The human Cu/Zn SOD analog produced differs from natural human Cu/Zn SOD in that the amino terminus alanine is not acetylated, as we have demonstrated by amino acid sequencing stoichiometry. The natural human SOD is acetylated at the amino terminus alanine (references 4–7). Furthermore, the natural human SOD is glycosylated (W. Huber, U.S. Pat. No. 3,579,495, May 18, 1971) while bacterial produced human SOD is unlikely to be glycosylated, as E. coli does not glycosylate its proteins. The amino acid sequence of the bacterially produced SOD analog is identical to that of mature human SOD, and does not contain a methionine residue at its N-terminus. The amount of authentic SOD produced by pSODβ1 was about 3-8% of the total protein produced by the bacteria as calculated from scanning of Coomasie stained SDS polyacrylamide gels (Table 1). The methods used to grow the strain recover the SOD produced and purify it are the same as those described for pSODβ1T11 in Example 2.

III. pSODβ1T11

The construction of pSODβ1T11 is shown in FIG. 15 and described in the Description of the Figures. The β-lactamase gene of pSODβ1 was replaced with the gene coding for tetracycline resistance derived from pBR322.

The amount of SOD analog produced by pSODβ1T11 was about 8-13% of the total protein produced by the bacteria as calculated from scanning of Coomasie stained SDS polyacrylamide gels (Table 1). The SOD analog produced is identical to that produced by pSODβ1.

IV. pSODβ1-BA2 is shown in FIG. 17 and described in the Description of the Figures. The CII RBS of pSODα13 was replaced by a synthetic DNA fragment with the sequence:

AATTCAATAATATTGAAAAAGGAAGAG
GTTATTATAACTTTTTCCTTCTCAT which is similar to the sequence of the natural β-lactamase RBS.

pSODβ1BA2 was introduced into E. coli strain A1645 by transformation using methods known to those of ordinary skill in the art. The clones obtained produce upon growth and induction an analog of human SOD. The amount of authentic SOD produced by pSODβ1-BA2 was about 2-4% of the total protein produced by the bacteria as calculated from scanning of Coomasie stained SDS polyacrylamide gel (Table 1). The SOD analog produced is identical to that produced by pSODβ1.

V. pSODβ1TT-1

The construction of pSODβ1TT-1 is shown in FIG. 16 and described in the Description of the Figures. The plasmid pSODβ1TT-1 was obtained by insertion of the $T_1T_2$ termination sequences at the 3' end of the SOD gene found in pSODβ1T11 (FIG. 15).

The plasmid pSODβ1TT-1 was introduced into E. coli strain A1645 by transformation using known methods. The strains produce upon growth an SOD analog. The amount of SOD analog produced was about 10-15% of the total protein produced by the bacteria as calculated from scanning of Coomasie stained SDS ployacrylamide gels. The SOD analog produced is identical to that produced by SODβ1.

The methods used to grow the strain, recover the SOD analog produced and purify it, are the same as those described for pSODβ1T11 in Example 2.

The level of expression was higher than that obtained from pSODβ1T11 (Table 1), probably due to a reduction in transcription and translation of non-desired DNA sequences.

TABLE 1

| | SOD Expression Levels | | | |
|---|---|---|---|---|
| Plasmid | Vector | RBS | % SOD[3] | Remarks |
| pSODα2 | pJH200 | cII | 0.1-0.3 | $Amp^R$ |
| pSODβ1 | pJH200 | BLA[1] | 3-8 | $Amp^R$ |
| pSODβ1T11 | pJH200 | BLA[1] | 8-13 | $Tet^R$ |
| pSODβ1TT-1 | pJH200 | BLA[1] | 10-15 | $Tet^R$; $T_1T_2$ |

TABLE 1-continued

| | SOD Expression Levels | | | |
|---|---|---|---|---|
| Plasmid | Vector | RBS | % SOD[3] | Remarks |
| pSODβ₁BA2 | pJH200 | BLA[2] | 2-4 | Amp[R] |

[1]Promoter and ribomosal binding site of β-lactamase gene.
[2]Synthetic ribosomal binding site corresponding to that of the β-lactamase gene.
[3]Amount of SOD analog produced expressed as percentage of total bacterial protein.
Amp[R] = Ampicillin resistance
Tet[R] = Tetracycline resistance
T₁T₂ = Transcription termination sequences

EXAMPLE 2

Growth of Bacteria Containing pSODβ₁T11

I. Stock Cultures

Stock cultures of pSODβ₁T11 were grown on casein medium (see inoculum), then diluted twofold with freezing medium and stored at −80° C. Freezing medium contains:

| | |
|---|---|
| K₂HPO₄ | 6.3 gr |
| KH₂PO₄ | 1.8 gr |
| Na Citrate | 0.45 gr |
| MgSO₄.7H₂O | 0.09 gr |
| (NH₄)₂SO₄ | 0.9 gr |
| Glycerol | 44 gr |
| Per 500 ml | |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C., and approximately 200 r.p.m. If needed subsequent stages in inoculum propagation were carried out in stirred aerated fermenters. Sterile medium was innoculated with 2–10% flask culture, and incubated 15 hours at 30° C., pH 7±0.5 with agitation and aeration to maintain dissolved oxygen level above 20% air saturation.

III. Production

The production medium contains:

| | |
|---|---|
| Casein hydrolysate | 20 g/l |
| Yeast extract | 10 g/l |
| K₂HPO₄ | 2.5 g/l |
| MgSO₄.7H₂O | 1 g/l |
| NaCl | 5 g/l |
| Biotin | 0.1 mg/l |
| Thiamine | 1 mg/l |
| Trace elements solution | 3 ml/l |
| Tetracycline | 12.5 mg/l |

In some of the experiments we added:

| | |
|---|---|
| CuSO₄.5H₂O | 0.8 g/l |
| ZnSO₄.7H₂O | 10 mg/l |

Biotin, thiamine, and tetracycline in concentrated solutions were filter sterilized separately and added to the sterile production medium before inoculation. Sterile glucose solution was added initially to supply 10 g/l. At the induction step another 10 g/l of glucose was added.

The trace elements solution contains:

| | |
|---|---|
| FeCl₃ | 16 g/l |
| ZnCl₂.4H₂O | 2 g/l |
| CoCl₂.6H₂O | 2 g/l |
| Na₂MoO₄.2H₂O | 2 g/l |
| CaCl₂.2H₂O | 1 g/l |
| CuCl₂ | 1 g/l |
| H₃BO₃ | 0.5 g/l |
| Conc. HCl | 100 ml/l |

The medium is inoculated with 0.5–10% inoculum culture and incubated at 30° C. Agitation-aeration rates are set to maintain dissolved oxygen level above 20% air saturation. The pH is maintained at 7±0.2 with NH₃. Once cell concentration reaches about 3.5 g/l (OD₆₆₀=10) induction is started.

The temperature is raised to 42° C. and maintained at 42° C. for 1–5 hours. The cuture is then chilled, and cells are recovered by centrifugation for enzyme purification.

RECOVERY OF SOD

One and half kilograms of bacterial cells (wet cake) are suspended in 12 liters of 50 mM sodium phosphate (pH 7.8), in a Polytron (Kinematica) blender while controlling the speed to minimize foaming. The homogeneous suspension is continuously passed through a Dynomill cell disrupter KD5 (Willy, A. Bachofen, Basel). The homogeneous suspension of disrupted cells is sonicated using a continuous flow cell and centrifuged in a CEPA 101 centrifuge. The supernatant is heated for 2 hrs at 65° C., cooled and centrifuged as before. The clear supernatant is concentrated to 1 liter in a Millipore Pellicon ultrafiltration device using 10,000 molecular weight cutoff cassettes (type PTGC). The concentrated protein solution is passed through a DEAE-Sephacel column (2 Kg DEAE Sephacel) equilibrated with 150 mM sodium phosphate buffer (pH 7.8). The flow through solution is collected, concentrated and dialyzed in a Pellicon ultrafiltration device against 20 mM Tris-HCL, pH, 7.8 and then applied on to a QAE-Sepharose column equilibrated with 20 mM Tris-HCl buffer. The column is developed with a 20 mM Tris-HCl buffer, pH 7.8, and a salt gradient (0–200 mM NaCl). SOD containing fractions are collected, concentrated using a Pellicon ultrafiltration device, dialyzed against distilled water and then brought to 100 mM Sodium Acetate by adding 1M Sodium Acetate buffer, pH 4.8. The protein solution is then further separated on a CM-Sepharose column equilibrated with 100 mM sodium acetate buffer, pH 4.7. The column is developed using the same buffer and a salt gradient (100–500 mM NaCl). SOD containing fractions are collected, concentrated using a Pellicon ultrafiltration device and lyophilized.

EXAMPLE 3

Enzymatic Activity of SOD Produced by Bacteria

The purified human SOD (hSOD) produced by bacteria in Example 2 under standard growth conditions (that is without adding extra CuSO₄) possessed only 5% of enzymatic activity as compared to bovine Cu/Zn SOD. Analysis of the metal content reveals that the enzyme contains little Cu, and that is only 8% of the expected value. Furthermore, it seems that most of the Cu++ sites are replaced by Zn ions since the protein contains almost twice the Zn required. However, completely metal free apoprotein, prepared from the bacterially produced h-SOD, regains essentially full enzymatic activity upon reconstitution in solution. The solution contains both $Cu^{++}$ and $Zn^{++}$, each at a concentration of 1.2 mole ions per mole active site. (Table 2).

The data presented above suggested that the intracellular concentration of $Cu^{++}$ is limited and insufficient to saturate the h-SOD produced. In a series of experiments we have demonstrated that elavated $Cu^{++}$ concentrations in the growth medium caused increase in the specific activity of h-SOD. Indeed, *E. coli* grown in casein hydrolysate (Example 2) supplemented with 200 ppm $Cu^{++}$, produced, after induction, fully active h-SOD with the natural composition of metals, and full enzymatic activity (Table 2). Additional experiments have demonstrated the same effect when the amount of exogenous $Cu^{++}$ added ranged from 50-250 ppm. We have seen a similar effect with LB (Luria Broth) medium supplemented with 75 ppm $Cu^{++}$.

EXAMPLE 4

Amino Terminal Sequence of Bacterial Produced Human-SOD

The sequence of 5 amino acids at the amino terminus of purified SOD prepared as described in Example 2 was determined by Edmann degradation. The amino acid sequence is identical to the N-terminus of human Cu/Zn SOD, that is Ala-Thr-Lys-Ala-Val. This confirms the authenticity of the bacterial product. It seems therefore that the soluble hSOD is accessible to *E. coli* processing enzymes which remove the N-terminus methionine.

DISCUSSION

We have demonstrated that bacteria which are induced to produce large amounts of human SOD when grown on LB or casein hydrolysate media, produce an enzymatically inactive protein. The protein so produced can be activated by reconstituting and adding back the missing $Cu^{++}$, $Zn^{++}$ ions. Unexpectedly, the bacteria can be induced to produce enzymatically active human-SOD by growing on media which has been supplemented with $Cu^{++}$. While not wishing to be bound by theory, we believe that certain components of rich media (such as LB and casein hydrolysate), chelate most of the available copper, such that the bacteria do not have available enough free copper to fill all the sites in the SOD molecules, which are being produced at elevated levels. The addition of 50-250 ppm of $Cu^{++}$ ions to the media apparently raises the $Cu^{++}$ within the bacteria to levels which are sufficient to provide all the $Cu^{++}$ necessary for the overproduced human Cu/Zn SOD.

TABLE 2

Activity and Metal Content of SOD Preparations

| Protein | Mole/Active Site Cu | Zn | Activity u/mg |
|---|---|---|---|
| h-SOD[1] | 0.07 | 1.62 | 167 |
| Apo enzyme | 0.01 | 0.02 | 0 |
| Reconstituted SOD | 0.81 | 0.88 | 2931 |
| h-SOD[2] | 0.88 | 0.90 | 2730 |
| Bovine SOD | 0.97 | 1.01 | 2805 |
| h-SOD (Sigma) | | | 1606 |

[1]h-SOD prepared as described in Example 2. The medium used did not contain the added $Cu^{++}$ and $Zn^{++}$.
[2]h-SOD prepared as described in Example 2. The medium used did contain the added $Cu^{++}$ and $Zn^{++}$.

SOD concentrations were determined by the method of Lowry (15) using bovine serum albumin as standard. Activity measurement monitoring the inhibition of reduction of ferricytochrome-c were carried out as described by McCord and Fridovich (1). Cu and Zn content in pure SOD preparations was determined by atomic absorption. SOD-apo enzyme was prepared according to Weser and Hartmann (16) and reconstituted by simultaneous addition of Cu and Zn (17).

REFERENCES

1. McCord, J. M. and Fridovich, I. (1969) J. Biol. Chem. 244, 6049-6055.
2. Fridovich, I. (1979) in Advances in Inorganic Biochemistry, eds. Eichhorn, G. L. and Marzilli, L. G. (Elsevier/North Holland, New York), pp. 67-90.
3. Freeman, B. A. and Crapo, J. D. (1982) Laboratory Investigation 47, 412-426.
4. Steinman, H. M. (1982) in Superoxide Dismutase, ed. Oberley, L. W. (CRC Press, Florida), pp. 11-68.
5. Hartz, J. W. and Deutsch, H. F. (1972) J. Biol. Chem. 247, 7043-7050.
6. Jabusch, J. R., Farb, D. L. Kerschensteiner, D. A. and Deutsch, H. F. (1980) Biochemistry (1980) 19: 2310-2316.
7. Barra, D., Martini, F., Bannister, J. V., Schinina, M. W., Rotilio, W. H., Bannister, W. H. and Bossa, F. (1980) FEBS Letters 120, 53-56.
8. Lieman-Hurwitz, J., Dafni, N., Lavie, V. and Groner, Y. (1982) Proc. Natl. Acad. Sci. USA 79, 2808-2811.
9. Sherman, L., Dafni, N., Leiman-Hurwitz, J. and Groner, Y. (1983) Proc. Natl. Acad. Sci. USA 80, 5465-5469.
10. Oberley, L. W. and Buettner, G. R. (1979) Cancer Research 39, 1141-1149.
11. Huber, W. and Menander-Huber, K. B. (1980) Clinics in Rheum. Dis. 6, 465-498.
12. McCord, J. M. and Roy, R. S. (1982) Can. J. Physiol. Pharma. 60, 1346-1352.
13. Alvarez, J. G. and Storey, B. T. (1983) Biol. Reprod. 28, 1129-1136.
14. Talmasoff, J. M., Ono, T. and Cutler, R. G. (1980) Proc. Natl. Acad. Sci. USA 77, 2777-2781.
15. Lowry, O. H. Rosebrough, N. J., Farr, A. L. and Randall, R. J. (1951) J. Biol. Chem. 193, 265-275.
16. Weser, U. and Hartmann, H. J. (1971) FEBS Lett. 17, 78-80.
17. Jewett, S. L., Latrenta, G. S. and Beck, C. M. (1982) Arc. Biochem. Biophys. 215m 116-128.

What is claimed is:

1. A method of producing an enzymatically active polypeptide analog of human Cu/Zn superoxide dismutase having the identical amino acid sequence and activity of naturally occurring human Cu/Zn superoxide dismutase which comprises:

growing a culture of bacterial cells in a zinc containing production medium supplemented with a non-growth inhibiting amount of $Cu^{++}$ such that the final concentration of $Cu^{++}$ in the medium is greater than 2 ppm, wherein said cells contain and are capable of expressing DNA encoding the polypeptide analog of human Cu/Zn superoxide dismutase and wherein said culture is grown under suitable conditions such that the DNA is expressed and the polypeptide is produced in the bacterial cells; and recovering the enzymatically active analog of human Cu/Zn superoxide dismutase so produced.

2. A method as in claim 1, wherein the bacterial cell is an *Escherichia coli* cell.

3. A method as in claim 1 wherein said culture of bacterial cells has been transformed with a plasmid, wherein said plasmid contains the DNA sequence encoding said polypeptide analog of human Cu/Zn superoxide dismutase incorporated therein.

4. A method as in claim 1, wherein said production medium is a casein hydrolysate medium.

5. A method as in claim 1, wherein said production medium is LB medium.

6. A method as in claim 1, wherein said $Cu^{++}$ concentration is from about 50 to about 250 ppm.

7. A method as in claim 4, wherein said $Cu^{++}$ concentration is about 200 ppm.

8. A method as in claim 5, wherein said $Cu^{++}$ concentration is about 75 ppm.

9. A method as in claim 1, wherein said production medium is also supplemented with an amount of $Zn^{++}$ so that the concentration of $Zn^{++}$ in the medium is greater than about 2 ppm.

10. A method as in claim 9, wherein said production medium is supplemented with about 0.8 g/l $CuSO_4.5H_2O$ and about 10 mg/l $ZnSO_4.7H_2O$.

11. A method as in claim 3, wherein said plasmid is $pSOD\beta_1$, $pSOD\alpha 2$, $pSOD\beta_1 T11$, $pSOD\beta_1$-BA2 or $pSOD\beta_1 TT$-1.

12. A method as in claim 1, wherein said bacterial cell is *Escherichia coli* strain A2097 containing plasmid pSODα2 ATCC 39786.

13. A method of recovering purified enzymatically active human Cu/Zn superoxide dismutase analog of claim 1 which comprises:
  (a) isolating the bacterial cells from the production medium;
  (b) disrupting the bacterial cells so as to form a suspension comprising cell debris and a protein supernatant solution;
  (c) separating said cell debris from the soluble protein supernatant solution;
  (d) heating said separated protein supernatant at about 65° C. for about 2 hours;
  (e) cooling the heated protein supernatant;
  (f) separating the resulting protein supernatant so as to produce a clear supernatant protein solution containing the superoxide dismutase thereof analog thereof; and
  (g) recovering the enzymatically active human Cu/Zn superoxide dismutase analog from the clear supernatant protein solution.

14. The method of claim 13, wherein the recovery of the enzymatically active human Cu/Zn superoxide dismutase analog from the clear supernatant protein solution further comprises:
  (a) treating the clear supernatant protein solution to obtain a concentrated solution of the superoxide dismutase analog;
  (b) subjecting the concentrated solution to both anion and cation exchange chromatography; and
  (c) collecting the resulting fractions containing purified superoxide dismutase analog thereof.

15. A method of producing an enzymatically active polypeptide analog of human Cu/Zn superoxide dismutase having the identical amino acid sequence and activity of naturally occurring human Cu/Zn superoxide dismutase which comprises:
  growing a culture of cells of a strain of *E. coli* in a zinc containing production medium supplemented with an amount of $Cu^{++}$ such that the final concentration of $Cu^{++}$ in the medium is greater than 2 ppm wherein said cells contain a plasmid capable of expressing DNA encoding a polypeptide analog of human Cu/Zn superoxide dismutase, and wherein said plasmid is selected from the group consisting of $pSOD\beta_1 T_{11}$, $pSOD\beta_1$, $pSOD\beta_1 TT$-1 and $pSOD\beta_1$-BA2; and recovering said polypeptide analog from the *E. coli* cells so cultured.

* * * * *